(12) United States Patent
Abe

(10) Patent No.: US 11,350,910 B2
(45) Date of Patent: Jun. 7, 2022

(54) ULTRASOUND DIAGNOSIS APPARATUS, MEDICAL IMAGE PROCESSING APPARATUS, AND MEDICAL IMAGE PROCESSING METHOD

(71) Applicant: CANON MEDICAL SYSTEMS CORPORATION, Otawara (JP)

(72) Inventor: Yasuhiko Abe, Otawara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 252 days.

(21) Appl. No.: 15/940,004

(22) Filed: Mar. 29, 2018

(65) Prior Publication Data
US 2018/0279997 A1 Oct. 4, 2018

(30) Foreign Application Priority Data

Mar. 31, 2017 (JP) .............................. JP2017-071980

(51) Int. Cl.
*A61B 8/08* (2006.01)
*G06T 7/246* (2017.01)
*G06T 7/00* (2017.01)

(52) U.S. Cl.
CPC .......... *A61B 8/5207* (2013.01); *A61B 8/0883* (2013.01); *A61B 8/5223* (2013.01);
(Continued)

(58) Field of Classification Search
CPC ........ G06T 2207/30048; G06T 7/0016; G06T 7/246; G06T 2207/10136;
(Continued)

(56) References Cited

U.S. PATENT DOCUMENTS 8,560,968 B1* 10/2013 Nair ...................... G16H 30/40
715/839
2012/0123267 A1* 5/2012 Dow ................... G01S 15/8993
600/443
(Continued)

FOREIGN PATENT DOCUMENTS

JP 2014-121541 7/2014

OTHER PUBLICATIONS

Knight et al. 2015 J. Am. Soc. Echocardiogr. 28:363-74 (Year: 2015).*

(Continued)

*Primary Examiner* — Keith M Raymond
*Assistant Examiner* — Patrick M Mehl
(74) *Attorney, Agent, or Firm* — Oblon, McClelland, Maier & Neustadt, L.L.P.

(57) ABSTRACT

In an ultrasound diagnosis apparatus according to an embodiment, processing circuitry obtains volume data corresponding to at least one cardiac cycle and being taken of a region including the right ventricle of a patient. The processing circuitry estimates motion information of a tissue in the region by using the volume data. The processing circuitry calculates information including at least one selected from between wall motion information and volume information related to the right ventricle, on the basis of the motion information of the tissue. The processing circuitry outputs the calculated information. The processing circuitry corrects first motion information of the right ventricular outflow tract, which is an outflow tract of the right ventricle, by using second motion information of a site that is positioned in the vicinity of the right ventricular outflow tract and exhibits motion similar to that of the right ventricular outflow tract.

15 Claims, 10 Drawing Sheets

(52) U.S. Cl.
CPC ............ *G06T 7/0016* (2013.01); *G06T 7/246* (2017.01); *A61B 8/488* (2013.01); *A61B 8/5238* (2013.01); *A61B 8/5276* (2013.01); *G06T 2207/10132* (2013.01); *G06T 2207/10136* (2013.01); *G06T 2207/30048* (2013.01)

(58) Field of Classification Search
CPC ........ G06T 2207/10132; A61B 8/5207; A61B 8/5223; A61B 8/0883; A61B 8/5276; A61B 8/488; A61B 8/5238; G16H 50/30
See application file for complete search history.

(56) References Cited

U.S. PATENT DOCUMENTS

| | | | |
|---|---|---|---|
| 2012/0165674 A1* | 6/2012 | Abe | ................... A61B 8/0883 600/443 |
| 2013/0184570 A1* | 7/2013 | Wang | .................... A61B 5/055 600/425 |
| 2015/0038846 A1* | 2/2015 | Abe | ........................ A61B 8/06 600/443 |
| 2015/0257731 A1 | 9/2015 | Abe | |

OTHER PUBLICATIONS

Gabbert et al. 2013 Mag. Res. In Med. 70:1718-1727 (Year: 2013).*
Lemmo et al. 2010 Computing in Cardiology 37:805-808 (Year: 2010).*
JS McGhie, et al. "A Novel 13-Segment Standardized Model for Assessment of Right Ventricular Function Using Two-Dimensional iRotate Echocardiography", Echocardiography, 2015, 33: 3 pages.
Akiko Atsumi, et al. "Right Ventricular Deformation Analyses Using a Three-Dimensional Speckle-Tracking Echocardiographic System Specialized for the Right Ventricle", Journal of the American Society of Echocardiography, 2016, 29(5):12 pages.

* cited by examiner

B-plane in RV-3DT
(RV coronal-view)

ULTRASOUND DIAGNOSIS APPARATUS, MEDICAL IMAGE PROCESSING APPARATUS, AND MEDICAL IMAGE PROCESSING METHOD

CROSS-REFERENCE TO RELATED APPLICATIONS

This application is based upon and claims the benefit of priority from Japanese Patent Application No. 2017-071980, filed on Mar. 21, 2017; the entire contents of which are incorporated herein by reference.

FIELD

Embodiments described herein relate generally to an ultrasound diagnosis apparatus, a medical image processing apparatus, and a medical image processing method.

BACKGROUND

Conventionally, to objectively and quantitatively evaluate functions of a site (e.g., an organ such as the heart) of an examined subject (hereinafter, "patient"), various types of techniques for analyzing three-dimensional video data taken of such a site have been proposed. For example, to evaluate cardiac functions, ultrasound diagnosis apparatuses can perform Wall Motion Tracking (WMT) processes to analyze motion of cardiac walls.

During a WMT process, for example, a tracking process that uses a pattern matching process on a local region is performed on three-dimensional video data of the heart acquired by using a body-surface ultrasound probe. As a result, analysis results are output to indicate myocardial strain of the left ventricle and/or the right ventricle of the heart, or the like.

In this situation, when the right ventricle is observed by implementing an apical approach method while using a body-surface ultrasound probe, there are certain locations where the observation is easy and certain locations where the observation is difficult. For example, the right ventricular outflow tract is known to be a location where the observation is difficult. In actual examples where visibility of the heart was studied by rotating a scanned plane while using a two-dimensional array ultrasound probe capable of acquiring three-dimensional data, visibility rates of the right ventricular outflow tract were 23% for normal subjects and 75% for diseased subjects. It is reported that rendering the right ventricular outflow tract is difficult especially for normal subjects. Accordingly, when motion of the right ventricle is analyzed by using three-dimensional video data acquired by a body-surface ultrasound probe, the quality of the analysis on the right ventricular outflow tract is degraded with high frequency.

BRIEF DESCRIPTION OF THE DRAW

DETAILED DESCRIPTION

An ultrasound diagnosis apparatus according to an embodiment includes processing circuitry. The processing circuitry is configured to obtain volume data corresponding to at least one cardiac cycle and being taken of a region including the right ventricle of a patient. The processing circuitry is configured to estimate motion information of a tissue in the region by using the volume data. The processing circuitry is configured to calculate information including at least one selected from between wall motion information and volume information related to the right ventricle, on the basis of the motion information of the tissue. The processing circuitry is configured to output the calculated information. The processing circuitry corrects first motion information of the right ventricular outflow tract, which is an outflow tract of the right ventricle, by using second motion information of a site that is positioned in the vicinity of the right ventricular outflow tract and exhibits motion similar to that of the right ventricular outflow tract.

Exemplary embodiments of an ultrasound diagnosis apparatus, a medical image processing apparatus, and a medical image processing method will be explained below, with reference to the accompanying drawings.

First Embodiment

Figure 1:
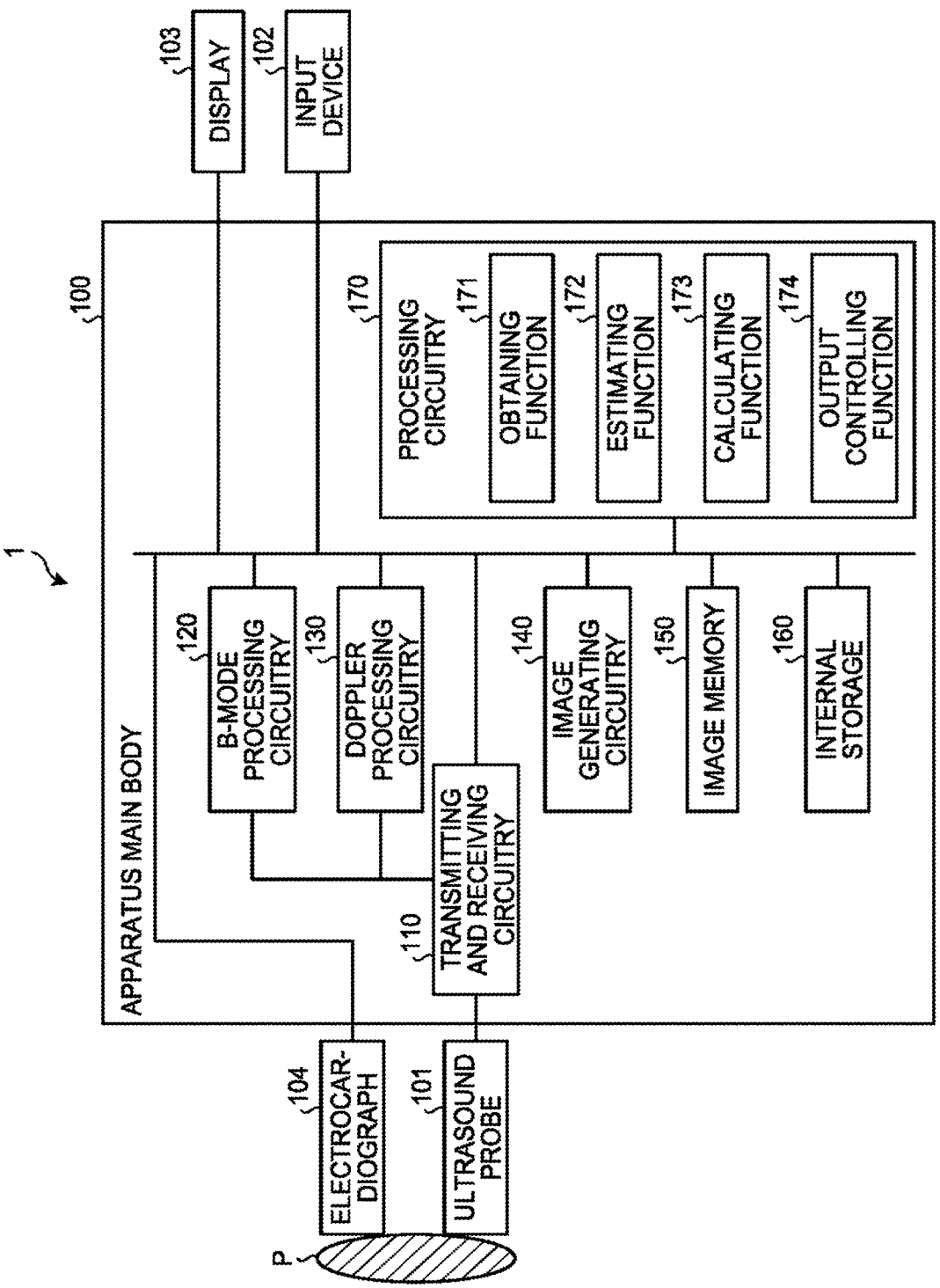
FIG. 1 is a block diagram illustrating an exemplary configuration of an ultrasound diagnosis apparatus according to a first embodiment.

FIG. 1 is a block diagram illustrating an exemplary configuration of an ultrasound diagnosis apparatus 1 according to a first embodiment. As illustrated in FIG. 1, the ultrasound diagnosis apparatus 1 according to the first embodiment includes an apparatus main body 100, an ultrasound probe 101, an input device 102, a display 103, and an electrocardiograph 104. The ultrasound probe 101, the input device 102, the display 103, and the electrocardiograph 104 are connected to one another so as to be able to communicate with the apparatus main body 100.

The ultrasound probe 101 includes a plurality of piezoelectric transducer elements. Each of the plurality of piezoelectric transducer elements is configured to generate an ultrasound wave on the basic of a drive signal supplied thereto from transmitting and receiving circuitry 110 included in the apparatus main body 100. Further, the ultrasound probe 101 is configured to receive a reflected wave from a patient P and to convert the received reflected wave into an electrical signal. Further, the ultrasound probe 101 includes matching layers provided for the piezoelectric transducer elements, as well as a backing member or the like that prevents ultrasound waves from propagating rearward from the piezoelectric transducer elements. In this situation, the ultrasound probe 101 is detachably connected to the apparatus main body 100.

When an ultrasound wave is transmitted from the ultrasound probe 101 to the patient P, the transmitted ultrasound wave is repeatedly reflected on a surface of discontinuity of acoustic impedances at a tissue in the body of the patient P and is received as a reflected-wave signal by each of the plurality of piezoelectric transducer elements included in the ultrasound probe 101. The amplitude of the reflected-wave signal is dependent on the difference between the acoustic impedances on the surface of discontinuity on which the ultrasound wave is reflected. When a transmitted ultrasound pulse is reflected on the surface of a moving blood flow, a cardiac wall, or the like, the reflected-wave signal is, due to the Doppler effect, subject to a frequency shift, depending on a velocity component of the moving members with respect to the ultrasound wave transmission direction.

For example, in the first embodiment, to scan the patient P three-dimensionally, a mechanical four-dimensional (4D) probe or two-dimensional (2D) array probe is connected as the ultrasound probe 101 to the apparatus main body 100. The mechanical 4D probe is capable of performing a two-dimensional scan by using a plurality of piezoelectric transducer elements that are arranged in a row like in a one-dimensional (1D) array probe and is also capable of performing a three-dimensional scan by swinging the plurality of piezoelectric transducer elements by a predetermined angle (a swing angle). Further, the 2D array probe is capable of performing a three-dimensional scan by using a plurality of piezoelectric transducer elements that are arranged in a matrix formation and is also capable of performing a two-dimensional scan by transmitting and receiving ultrasound waves in a converged manner.

The input device 102 includes a mouse, a keyboard, a button, a panel switch, a touch command screen, a foot switch, a trackball, a joystick, and/or the like. The input device 102 is configured to receive various types of setting requests from an operator of the ultrasound diagnosis apparatus 1 and to transfer the received various types of setting requests to the apparatus main body 100.

The display 103 is configured to display a Graphical User Interface (GUI) used by the operator of the ultrasound diagnosis apparatus 1 to input the various types of setting requests through the input device 102 and to display ultrasound image data generated by the apparatus main body 100 or the like. Further, to inform the operator of processing statuses of the apparatus main body 100, the display 103 is configured to display various types of messages. Further, the display 103 includes a speaker and is also capable of outputting audio. For example, to inform the operator of the processing statuses of the apparatus main body 100, the speaker included in the display 103 is configured to output a predetermined sound such as a beep sound.

The electrocardiograph 104 is configured to obtain an electrocardiogram (ECG) of the patient P, as a biological signal of the patient P. The electrocardiograph 104 transmits the obtained electrocardiogram to the apparatus main body 100. In the first embodiment, an example will be explained in which the electrocardiograph 104 is used as a means for obtaining information about cardiac phases of the heart of the patient P; however, possible embodiments are not limited to this example.

The apparatus main body 100 is an apparatus configured to generate ultrasound image data on the basis of the reflected-wave signals received by the ultrasound probe 101. The apparatus main body 100 illustrated in FIG. 1 is an apparatus capable of generating three-dimensional ultrasound image data on the basis of three-dimensional reflected-wave data received by the ultrasound probe 101. The three-dimensional ultrasound image data is an example of either "three-dimensional medical image data" or "volume data".

As illustrated in FIG. 1, the apparatus main body 100 includes the transmitting and receiving circuitry 110, B-mode processing circuitry 120, Doppler processing circuitry 130, image generating circuitry 140, an image memory 150, internal storage 160, and processing circuitry 170. The transmitting and receiving circuitry 110, the B-mode processing circuitry 120, the Doppler processing circuitry 130, the image generating circuitry 140, the image memory 150, the internal storage 160, and the processing circuitry 170 are connected to one another so as to be able to communicate with one another.

The transmitting and receiving circuitry 110 includes a pulse generator, a transmission delay unit, a pulser, and the like and is configured to supply the drive signal to the ultrasound probe 101. The pulse generator is configured to repeatedly generate a rate pulse used for forming a transmission ultrasound wave, at a predetermined rate frequency. The transmission delay unit is configured to apply a transmission delay period that is required to converge the ultrasound wave generated by the ultrasound probe 101 into the form of a beam and to determine transmission directionality and that corresponds to each of the piezoelectric transducer elements, to each of the rate pulses generated by the pulse generator. Further, the pulser is configured to apply the drive signal (a drive pulse) to the ultrasound probe 101 with timing based on the rate pulses. In other words, by varying the delay periods applied to the rate pulses, the transmission delay unit is able to arbitrarily adjust the transmission directions of the ultrasound waves transmitted from the surfaces of the piezoelectric transducer elements.

The transmitting and receiving circuitry 110 has a function that is able to instantly change the transmission frequency, the transmission drive voltage, and the like, for the purpose of executing a predetermined scanning sequence on the basis of an instruction from the processing circuitry 170 (explained later). In particular, the function to change the transmission drive voltage is realized by using linear-amplifier-type transmission circuitry of which the value can be instantly switched or by using a mechanism configured to electrically switch between a plurality of power source units.

Further, the transmitting and receiving circuitry 110 includes a pre-amplifier, an Analog/Digital (A/D) converter, a reception delay unit, an adder, and the like and is configured to generate the reflected-wave data, by performing various types of processes on the reflected-wave signals received by the ultrasound probe 101. The pre-amplifier is configured to amplify the reflected-wave signal for each of the channels. The A/D converter is configured to perform an A/D conversion on the amplified reflected-wave signals. The reception delay unit is configured to apply a delay period required to determine reception directionality thereto. The adder is configured to generate the reflected-wave data by performing an adding process on the reflected-wave signals processed by the reception delay unit. As a result of the adding process performed by the adder, reflected components from the direction corresponding to the reception directionality of the reflected-wave signals are emphasized. A comprehensive beam for the ultrasound transmission and reception is formed according to the reception directionality and the transmission directionality.

When scanning a three-dimensional region of the patient P, the transmitting and receiving circuitry 110 causes the ultrasound probe 101 to transmit an ultrasound beam in a three-dimensional direction. Further, the transmitting and receiving circuitry 110 generates three-dimensional reflected-wave data from the reflected-wave signals received by the ultrasound probe 101.

The B-mode processing circuitry 120 is configured to generate data (P-mode data) in which signal intensities are expressed by degrees of brightness, by receiving the reflected-wave data from the transmitting and receiving circuitry 110 and performing a logarithmic amplification, an envelope detection process, and/or the like thereon.

The Doppler processing circuitry 130 is configured to generate data (Doppler data) obtained by extracting moving member information such as velocity, dispersion, power, and the like with respect to multiple points, by performing a frequency analysis to obtain velocity information from the reflected-wave data received from the transmitting and receiving circuitry 110 and extracting blood flows, tissues, contrast agent echo components based on the Doppler effect.

The B-mode processing circuitry 120 and the Doppler processing circuitry 130 illustrated in FIG. 1 are each capable of processing both two-dimensional reflected-wave data and three-dimensional reflected-wave data. In other words, the B-mode processing circuitry 120 is configured to generate two-dimensional B-mode data from two-dimensional reflected-wave data and to generate three-dimensional B-mode data from three-dimensional reflected-wave data. Further, the Doppler processing circuitry 130 is configured to generate two-dimensional Doppler data from two-dimensional reflected-wave data and to generate three-dimensional Doppler data from three-dimensional reflected-wave data.

The image generating circuitry 140 is configured to generate ultrasound image data from the data generated by the B-mode processing circuitry 120 and the Doppler processing circuitry 130. In other words, the image generating circuitry 140 is configured to generate two-dimensional B-mode image data in which intensities of the reflected waves are expressed by degrees of brightness, from the two-dimensional B-mode data generated by the B-mode processing circuitry 120. Further, the image generating circuitry 140 is configured to generate two-dimensional Doppler image data expressing the moving member information from the two-dimensional Doppler data generated by the Doppler processing circuitry 130. The two-dimensional Doppler image data represents a velocity image, a dispersion image, a power image, or an image combining any of these. Further, the image generating circuitry 140 is also capable of generating M-mode image data from time-series data of B-mode data on one scanning line generated by the B-mode processing circuitry 120. Further, the image generating circuitry 140 is also capable of generating a Doppler waveform plotting the velocity information of a blood flow or a tissue in a time series, from the Doppler data generated by the Doppler processing circuitry 130.

In this situation, generally speaking, the image generating circuitry 140 converts (by performing a scan convert process) a scanning line signal sequence from an ultrasound scan into a scanning line signal sequence in a video format used by, for example, television and generates display-purpose ultrasound image data. More specifically, the image generating circuitry 140 generates the display-purpose ultrasound image data by performing a coordinate transformation process compliant with the ultrasound scanning mode used by the ultrasound probe 101. Further, as various types of image processing processes besides the scan convert process, the image generating circuitry 140 performs, for example, an image processing process (a smoothing process) to re-generate a brightness average value image, an image processing process (an edge enhancement process) that uses a differential filter inside an image, or the like, by using a plurality of image frames resulting from the scan convert process. Also, the image generating circuitry 140 combines text information of various parameters, scale graduations, body marks, and the like with the ultrasound image data.

In other words, the B-mode data and the Doppler data are each ultrasound image data before the scan convert process. The data generated by the image generating circuitry 140 is the display-purpose ultrasound image data after the scan convert process. The B-mode data and the Doppler data may be referred to as raw data.

Further, the image generating circuitry 140 generates three-dimensional B-mode image data by performing a coordinate transformation process on the three-dimensional B-mode data generated by the B-mode processing circuitry 120. Further, the image generating circuitry 140 generates three-dimensional Doppler image data by performing a coordinate transformation process on the three-dimensional Doppler data generated by the Doppler processing circuitry 130. In other words, the image generating circuitry 140 generates "the three-dimensional B-mode image data and the three-dimensional Doppler image data" each as "three-dimensional ultrasound image data (volume data)".

Further, to generate various types of two-dimensional image data used for displaying the volume data on the display 103, the image generating circuitry 140 performs a rendering process on the volume data. An example of the rendering process performed by the image generating circuitry 140 is a process of generating Multi Planar Reconstruction (MPR) image data from the volume data by implementing an MPR method. Other examples of the rendering process performed by the image generating circuitry 140 include a process of performing a "Curved MPR" process on the volume data and a process of performing a "Maximum Intensity Projection" process on the volume data. Other examples of the rendering process performed by the image generating circuitry 140 include a Volume Rendering (VR) process and a Surface Rendering (SR) process.

The image memory 150 is a memory configured to store therein the display-purpose image data generated by the image generating circuitry 140. Further, the image memory 150 is also capable of storing therein any of the data generated by the B-mode processing circuitry 120 and the Doppler processing circuitry 130. After a diagnosis process, for example, the operator is able to invoke any of the B-mode data and the Doppler data stored in the image memory 150. The invoked B-mode data and Doppler-data can serve as display-purpose ultrasound image data after being routed through the image generating circuitry 140.

The image generating circuitry 140 stores, into the image memory 150, ultrasound image data and the time at which an ultrasound scan was performed to generate the ultrasound image data, so as to be kept in correspondence with an electrocardiogram transmitted thereto from the electrocardiograph 104. By referring to the data stored in the image memory 150, the processing circuitry 170 (explained later) is able to obtain the cardiac phases during the ultrasound scan performed to generate the ultrasound image data.

The internal storage 160 is configured to store therein control programs for performing ultrasound transmissions and receptions, image processing processes, and display processes as well as various types of data such as diagnosis information (e.g., patient's IDs, medical doctors' observations), diagnosis protocols, various types of body marks, and the like. Further, the internal storage 160 may be used, as necessary, for saving therein any of the image data stored in the image memory 150. Further, the data stored in the internal storage 160 may be transferred to an external apparatus via an interface (not illustrated). Examples of the external apparatus include a Personal Computer (PC) used by a medical doctor who performs an image diagnosis process, a storage medium such as a Compact Disk (CD) or a Digital Versatile Disk (DVD), a printer, or the like.

The processing circuitry 170 is configured to control the overall processes performed by the ultrasound diagnosis apparatus 1. More specifically, the processing circuitry 170 is configured to control processes performed by the transmitting and receiving circuitry 110, the B-mode processing circuitry 120, the Doppler processing circuitry 130, and the image generating circuitry 140, on the basis of the various types of setting requests input by the operator via the input device 102 and the various types of control programs and various types of data read from the internal storage 160. Further, the processing circuitry 170 is configured to exercise control so that the display 103 displays any of the display-purpose ultrasound image data stored in the image memory 150 and the internal storage 160.

Further, the processing circuitry 170 is configured to execute an obtaining function 171, an estimating function 172, a calculating function 173, and an output controlling function 174. In this situation, the obtaining function 171 is an example of an obtaining unit. The estimating function 172 is an example of an estimating unit. The calculating function 173 is an example of a calculating unit. The output controlling function 174 is an example of an output controlling unit. The contents of processes performed by the obtaining function 171, the estimating function 172, the calculating function 173, and the output controlling function 174 executed by the processing circuitry 170 will be explained later.

In this situation, for example, processing functions performed by the constituent elements of the processing circuitry 170 illustrated in FIG. 1, namely the obtaining function 171, the estimating function 172, the calculating function 173, and the output controlling function 174, are recorded in the internal storage 160 in the form of computer-executable programs. The processing circuitry 170 is a processor configured to realize the functions corresponding to the programs by reading and executing the programs from the internal storage 160. In other words, the processing circuitry 170 that has read the programs has the functions illustrated within the processing circuitry 170 in FIG. 1.

In the first embodiment, the example is explained in which the single processing circuit (i.e., the processing circuitry 170) realizes the processing functions described below. However, another arrangement is also acceptable in which processing circuitry is structured by combining together a plurality of independent processors, so that the functions are realized as a result of the processors executing the programs.

Next, a Wall Motion Tracking (WMT) process performed by the ultrasound diagnosis apparatus 1 according to the first embodiment will be explained. In the following sections, an example will be explained in which the processing circuitry 170 analyzes motion of cardiac walls by performing a WMT process that uses three-dimensional images (3DWMT); however, possible embodiments are not limited to this example. For instance, the processing circuitry 170 is capable of not only performing the wall motion tracking process, but also calculating volume information related to the volume of the heart.

The obtaining function 171 is configured to obtain volume data corresponding to at least one cardiac cycle and being taken of a region including the right ventricle of the patient P. For example, the obtaining function 171 obtains three-dimensional medical image data that is taken of the heart of the patient P and corresponds to at least one heartbeat.

For example, the operator takes moving image data represented by three-dimensional ultrasound image data rendering myocardia, by performing a three-dimensional scan on a region including the heart of the patient P, while using a sector probe. The moving image data is, for example, a group of ultrasound image data including ultrasound image data corresponding to each temporal phase and having been acquired as brightness-level signals in the B-mode. In this situation, the "temporal phase" denotes an arbitrary point in time (a time) in the cyclic motion of the heart and may also be referred to as a "cardiac phase".

Further, the image generating circuitry 140 is configured to generate moving image data of the right ventricle of the heart and to store the generated moving image data into the image memory 150. After that, as a processing target section, for example, the operator sets a section corresponding to one heartbeat from an R-wave to the immediately following R-wave in an electrocardiogram. Alternatively, the first embodiment is also applicable to situations where the processing target section is arranged to be a section corresponding to two heartbeats or a section corresponding to three heartbeats.

Further, the obtaining function 171 is configured to obtain the group of ultrasound image data from the image memory 150, for example. The group of ultrasound image data includes three-dimensional ultrasound image data (volume data) in a plurality of frames contained in the section of one heartbeat set by the operator.

The estimating function 172 is configured to estimate motion information of the region including the right ventricle, by using the volume data. For example, at first, the estimating function 172 sets a region of interest (an initial contour) corresponding to the right ventricle with the volume data, by performing the processing procedure described below.

For example, the operator designates an arbitrary cardiac phase with respect to the group of volume data in a time series obtained by the obtaining function 171. In this situation, the designated arbitrary cardiac phase is an arbitrary frame among the frames contained in the section of the one heartbeat. For example, an end-diastolic phase (the first R-wave temporal phase) is most desirable. Further, when the operator has designated the arbitrary cardiac phase, the estimating function 172 sets the three-dimensional initial contour with the ultrasound image data corresponding to the designated cardiac phase.

In this situation, the three-dimensional initial contour is generated, for example, by performing an interpolating process on two-dimensional contour lines each of which is input with respect to a different one of a plurality of reference MPR cross-sectional planes. For example, the operator inputs a contour line indicating the contour of the endocardium of the right ventricle, with respect to each of the plurality of reference MPR cross-sectional planes. After that, the estimating function 172 transforms the position of the contour line input to each of the reference MPR cross-sectional planes, into coordinates in three-dimensional ultrasound image data. Subsequently, the estimating function 172 generates a three-dimensional contour shape (the initial contour) between the contour lines in the three-dimensional ultrasound image data, by performing a spatial interpolating process between the contour lines. In this manner, the estimating function 172 sets the initial contour of the endocardium of the right ventricle. Further, it is desirable to set an initial contour of the epicardium of the right ventricle to a position allowing a predetermined wall thickness (approximately 4 mm to 6 mm) from the plane of the endocardium.

Figure 2:
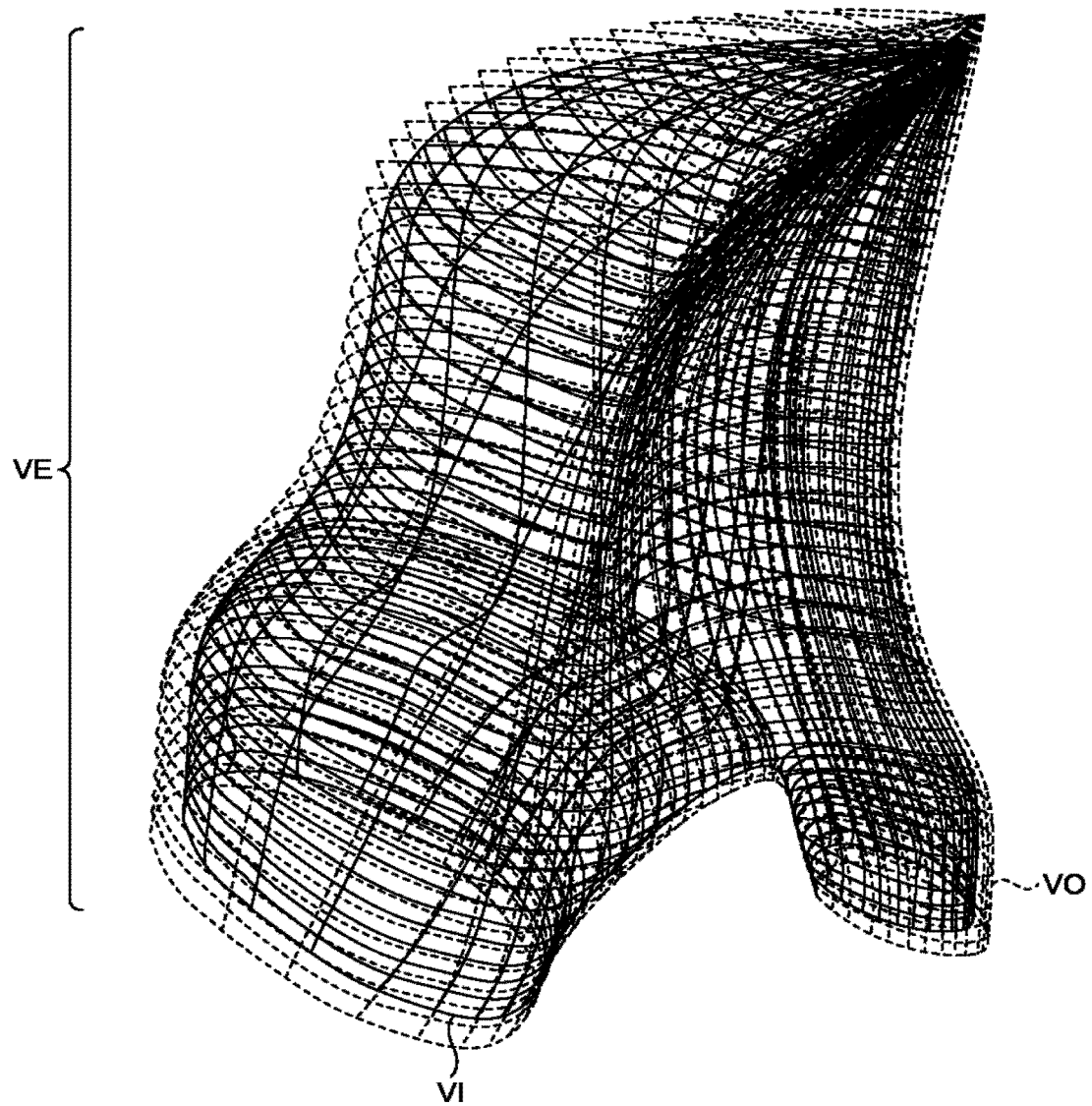
FIG. 2 is a drawing for explaining an initial contour set by an estimating function according to the first embodiment.

FIG. 2 is a drawing for explaining the initial contour set by the estimating function 172 according to the first embodiment. FIG. 2 illustrates an initial contour (VE) set with the right ventricle. In FIG. 2, the mesh structure indicated with solid lines corresponds to the initial contour (VI) set with the endocardium of the right ventricle. The mesh structure indicated with broken lines corresponds to the initial contour (VO) set with the epicardium of the right ventricle.

As illustrated in FIG. 2, within the ultrasound image data corresponding to the arbitrary cardiac phase, the estimating function 172 sets the three-dimensional initial contour (VE) in the position corresponding to the endocardium of the right ventricle. In this situation, intersection points of the mesh of the initial contour (VE) are constituent points structuring either an inner contour or an outer contour of the right ventricle. The intersection points correspond to tracking points that are chronologically tracked for the purpose of calculating motion information of the tissue.

Further, the estimating function 172 sets address numbers in a plurality of positions on the contour of the region of interest. For example, the estimating function 172 sets the address numbers with the plurality of constituent points structuring the initial contour (VE) that was set. The address numbers are numbers appended for the purpose of identifying the tracking points. For example, the address numbers are defined on the basis of the positions of the tracking points on the endocardium of the heart. The address numbers do not necessarily have to be numbers (numerals) and may be any identification information (e.g., characters, symbols, or the like) capable of identifying the positions of the tracking points.

For example, the estimating function 172 defines the positions of the constituent points of the endocardium of the heart as P_endo(t,h,d). In this situation, t denotes a frame (a cardiac phase) contained in the section of the one heartbeat, while h denotes an address number in the longitudinal direction (the height), and d denotes an address number in the circumferential direction (the azimuth). In the present example, because the initial cross-sectional plane is set by using the first R-wave temporal phase, t=0 is satisfied.

Further, as a reference position in the circumferential direction, the estimating function 172 sets, for example, an end part of the right ventricle positioned on the tricuspid valve side and determines the value of d at the constituent point in that position to be 0. In other words, the position of the constituent point in the reference position can be expressed as P_endo(0,h,0). Further, the estimating function 172 sequentially sets the address numbers d=0, 1, 2, 3 and so on with the constituent points in the circumferential direction, starting with the constituent point in the reference position. Further, from the three-dimensional initial contour, the estimating function 172 determines the position of an annular contour farthest from the cardiac apex to be a reference position in the longitudinal direction and determines the value of h at the constituent point in that position to be 0. In other words, the position of the constituent point in the reference position can be expressed as P_endo(0,0,d). Subsequently, the estimating function 172 sequentially sets the address numbers h=0, 1, 2, 3, and so on with the constituent points in the direction toward the cardiac apex, starting with the constituent point in the reference position.

In this manner, the estimating function 172 sets the plurality of constituent points (tracing points) having the address numbers appended thereto, in the positions corresponding to the endocardium of the right ventricle in the volume data. For setting the initial contour, possible methods are not limited to the manual operation described above. It is also acceptable to use another method by which the estimating function 172 automatically or semi-automatically detects the boundary in the image by using a dictionary database for endocardium contour shapes (a statistical database of contours that were set in the past, for example).

For example, the estimating function 172 tracks positions of the plurality of constituent points in the plurality of pieces of ultrasound image data included in the group of volume data, by performing a tracking process that includes a pattern matching process while using the volume data in the initial temporal phase in which the plurality of constituent points were set and the volume data in the subsequent temporal phase.

For example, when the plurality of constituent points are set in the positions corresponding to the initial contour, with respect to the volume data of the frame t=0 included in the group of volume data, the estimating function 172 tracks the positions of the constituent points in other frames t, by performing a process including pattern matching processes. More specifically, the estimating function 172 repeatedly performs the pattern matching processes between the volume data in a frame in which a plurality of constituent points have already been set and the volume data in the frame adjacent to the frame. In other words, the estimating function 172 tracks the positions of the constituent points P_endo(t,h,d) in the volume data in the frames corresponding to t=0, 1, 2, 3, and so on, starting with the constituent points P_endo(0,h,d) on the endocardium of the heart in the volume data corresponding to t=0. As a result, the estimating function 172 obtains coordinate information of the constituent points structuring the endocardium of the heart, with respect to each of the frames contained in the section of the one heartbeat.

After that, by using the positions of the plurality of constituent points in the plurality of pieces of ultrasound image data included in the group of volume data, the estimating function 172 calculates motion information indicating motion of the tissue for each of the pieces of ultrasound image data. The motion information calculated by the estimating function 172 is provided for the constituent points (the tracking points) used for the calculation. More specifically, for example, the motion information calculated from the constituent points of the endocardium of the heart is defined as V_endo(t,h,d). After that, the estimating function 172 stores the calculated motion information into the image memory 150.

As explained above, the estimating function 172 estimates the motion information of the right ventricle. Although the processes performed on the endocardium of the right ventricle have been explained in the present example, possible embodiments are not limited to this example. For instance, the processes described above may be performed not only on the endocardium, but on the epicardium or on an intermediate layer between the endocardium and the epicardium. Further, the estimating function 172 may perform the processes not only on the right ventricle, but on any other predetermined arbitrary region such as, for example, the left ventricle, the left atrium, the right atrium, the entire heart, or the like.

On the basis of the motion information of the tissue, the calculating function 173 is configured to calculate information including at least one selected from between wall motion information and volume information about the right ventricle. In this situation, typical examples of the wall motion information calculated by the calculating function 173 include a local myocardial displacement [mm] of each of the constituent points in each frame, a local myocardial strain value [%] indicating a rate of change in the distance between two points, or a temporal change in either of these values such as a local myocardial velocity value [cm/s] or a local myocardial train rate [1/s], for example. However, possible examples of the wall motion information are not limited to these parameters. It is possible to use any parameter that can be calculated by using the coordinate information of the plurality of constituent points in the frames. For example, a component separation may be applied to any of these pieces of wall motion information. For the right ventricle, for example, indices such as a Longitudinal Strain (LS) value obtained by separating the components in the longitudinal direction or a Circumferential Strain (CS) value obtained by separating the components in the circumferential direction may be used. These indices are calculated by implementing a two-dimensional speckle tracking method that uses a two-dimensional image (a long-axis image or a short-axis image) of the right ventricle. Further, while a three-dimensional speckle tracking method is implemented, a local Area Change (AC) ratio may be defined. Because the AC values do not require component separation processes, it is possible to perform stable analyses even on a complicated shape such as that of the right ventricle.

Further, examples of wall motion information that are often clinically used for evaluating functions of the right ventricle include a Tricuspid Annular Plane Systolic Excursion (TAPSE) value measured in the M-mode. Because the M-mode is for one-dimensional analyses, with the TAPSE value, a displacement component in the direction toward the ultrasound probe 101 is observed with respect to a section in the vicinity of the tricuspid valve ring. In contrast, by using a three-dimensional speckle tracking method, it is possible to obtain information of displacement that covers the entire region of the right ventricle. In that situation, as for the direction of the displacement, it is possible to detect a displacement component in a longitudinal direction or in a wall-thickness (radial) direction determined while using the region of interest (the right ventricle) as reference. Further, as an index that is not easily affected by the complicated shape of the right ventricle, it is also acceptable to use a moving distance D that involves no component separations in certain directions (D=sqrt ((Px(n)−Px(n0))^2+(Py(n)−Py(n0))^2+(Pz(n)−Pz(n0))^2)) where (Px(n),Py(n),Pz(n)) indicates the position of a tracking point P, while n denotes a temporal phase, and n0 denotes a reference temporal phase.

Further, the calculating function 173 is configured to calculate volume information as an index for the pumping function of the heart. For example, the calculating function 173 calculates volume information of a region of interest including the right ventricle. In this situation, the region for which the volume information is calculated by the calculating function 173 may be changed as appropriate.

In this manner, the calculating function 173 calculates the information including at least one selected from between the wall motion information and the volume information of the right ventricle, with respect to the group of ultrasound image data. The one or more types of parameters calculated by the calculating function 173 may be pre-set or may be selected by the operator as appropriate.

The output controlling function 174 is configured to output the calculated information. For example, the output controlling function 174 outputs the information including at least one selected from between the wall motion information and the volume information of the right ventricle that was calculated by the calculating function 173.

For example, the output controlling function 174 converts either the wall motion information or the volume information calculated by the calculating function 173 into color codes and further maps the color codes in a display image. Alternatively, the output controlling function 174 calculates an average value for each of the segments included in the region of interest, by using the wall motion information calculated for each of the constituent points. After that, the output controlling function 174 generates and displays a time-change curve of the calculated average values. As a result, the output controlling function 174 is able to provide a functional analysis of the right ventricle for each of the segments.

The output destination to which the information is output by the output controlling function 174 is not limited to the display 103. For example, the output controlling function 174 may transmit the information to an arbitrary apparatus connected thereto via a network. More specifically, the output controlling function 174 may transmit the information to a server apparatus that manages data in the hospital in a centralized manner or to an apparatus (e.g., a report creating apparatus) used for creating diagnosis reports. Further, for example, the output controlling function 174 may store the information into a recording medium such as a Digital Versatile Disk (DVD).

The WMT process performed by the ultrasound diagnosis apparatus 1 according to the first embodiment has thus been explained. However, when the right ventricle is observed by implementing an apical approach method while using a body-surface ultrasound probe, there are certain locations where the observation is easy and certain locations where the observation is difficult. For example, the right ventricular outflow tract is known to be a location where the observation is difficult. When an ultrasound scan is performed from the body surface, because the scan angle is large on the right ventricular outflow tract side and because the right ventricular outflow tract is positioned close to the ribs, the passage of ultrasound waves is limited with respect to the opening of the ultrasound probe. Further, because the ribs and the left lung (air), which do not pass ultrasound waves, are positioned very close to the surroundings of the right ventricular outflow tract, the signal intensities of the ultrasound waves are therefore attenuated, and the transmission/reception beam is not easily formed. Thus, it is considered that these factors make it difficult to observe the right ventricular outflow tract when a body-surface ultrasound probe is used.

In actual examples where visibility of the heart was studied by rotating the scanned plane while using a two-dimensional array ultrasound probe capable of acquiring three-dimensional data, visibility rates of the right ventricular outflow tract were 23% for normal subjects and 75% for diseased subjects. It is reported that rendering the right ventricular outflow tract is difficult especially for normal subjects. Accordingly, when the wall motion information of the right ventricle is analyzed by using three-dimensional video data acquired by a body-surface ultrasound probe, the quality of the analysis on the right ventricular outflow tract is degraded with high frequency.

To cope with this situation, the ultrasound diagnosis apparatus 1 according to the first embodiment performs the processes described below, for the purpose of improving the quality of the analyses performed on the motion of the right ventricular outflow tract. In other words, the ultrasound diagnosis apparatus 1 corrects motion information of the right ventricular outflow tract, by using motion information of a site that is positioned in the vicinity of the right ventricular outflow tract and exhibits motion similar to that of the right ventricular outflow tract. In the first embodiment, an example will be explained in which the crista supraventricularis is used as the site that is positioned in the vicinity of the right ventricular outflow tract and exhibits motion similar to that of the right ventricular outflow tract.

Figure 3:
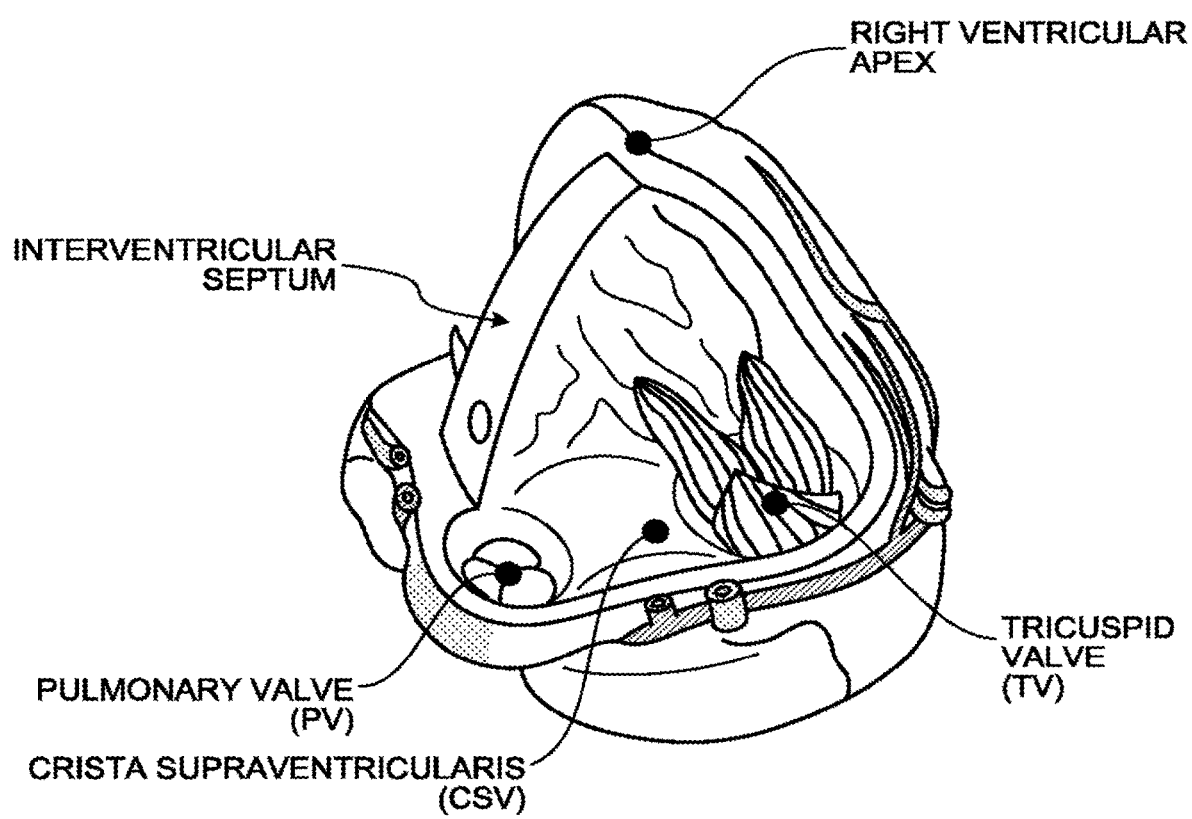
FIG. 3 is a drawing for explaining the crista supraventricularis.

FIG. 3 is a drawing for explaining the crista supraventricularis. FIG. 3 presents an anatomic model drawing illustrating the lumen of the right ventricle, while the right ventricle is unfolded from the free wall side. In FIG. 3, the right ventricular apex is depicted at the top; the interventricular septum is depicted on the far side; the tricuspid valve (TV) is depicted on the right; and the pulmonary valve (PV) is depicted on the left.

As illustrated in FIG. 3, the crista supraventricularis is positioned in a linking site that links the right ventricular inlet tract (Inlet) starting from the tricuspid valve, to the right ventricular outflow tract (RVOT) ending at the pulmonary valve and is considered to be a medial site that is neither an inflow tract nor an outflow tract. In the first embodiment, the crista supraventricularis is detected as an apex position of the linking site on the right ventricular lumen side.

As the inventors observed 3DWMT images of the right ventricle obtained from animal experiments with thoracotomy that were not impacted from the ribs or the lungs, as well as transesophageal echocardiography (TEE) probe images in which body surface tissues and the ribs were avoided, it was discovered that motion of the right ventricular outflow tract corresponds to motion of the crista supraventricularis. In other words, in clinical cases where motion of the right ventricular outflow tract was unsatisfactory due to degradation of the right heart functions, motion of the crista supraventricularis was also unsatisfactory. On the contrary, in clinical cases where motion of the right ventricular outflow tract was excellent, motion of the crista supraventricularis was also excellent. Further, because the crista supraventricularis is positioned farther from the ribs, the sternum, and the left lung, compared to the right ventricular outflow tract is, echo signals are more easily acquired from the crista supraventricularis than from the right ventricular outflow tract. For these reasons, in the first embodiment, the crista supraventricularis is used as the site that is positioned in the vicinity of the right ventricular outflow tract and exhibits motion similar to that of the right ventricular outflow tract.

The estimating function 172 according to the first embodiment is configured to correct first motion information of the right ventricular outflow tract, by using second motion information of a site that is positioned in the vicinity of the right ventricular outflow tract and exhibits motion similar to that of the right ventricular outflow tract. In the following sections, an example with processes performed on the endocardium of the right ventricle will be explained; however, possible embodiments are not limited to this example. For instance, the processes described below may be performed not only on the endocardium of the right ventricle, but on the epicardium or on an intermediate layer between the endocardium and the epicardium of the right ventricle.

Figure 4A:
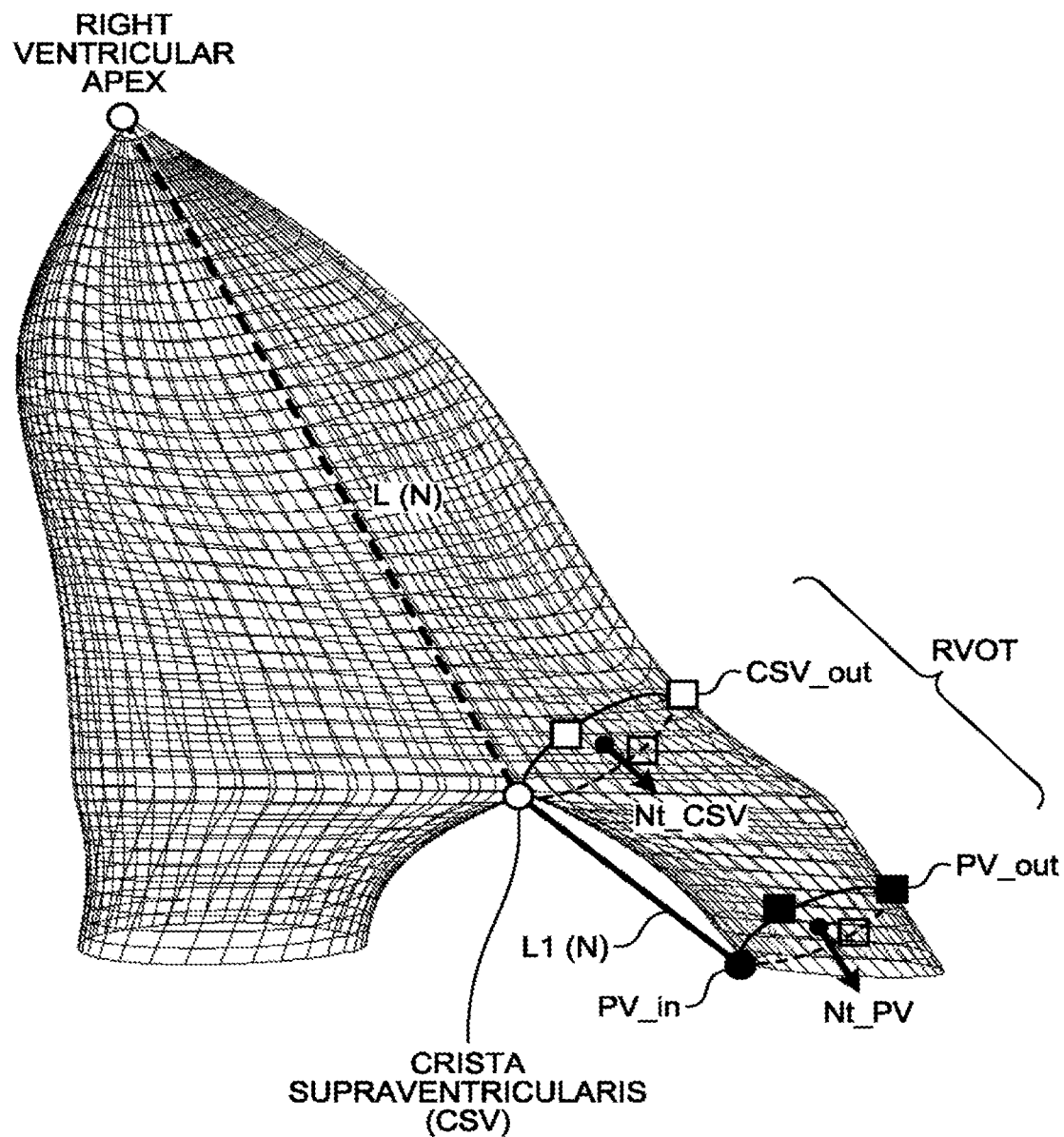
FIGS. 4A and 4B are drawings for explaining a process performed by the estimating function according to the first embodiment.
Figure 4B:
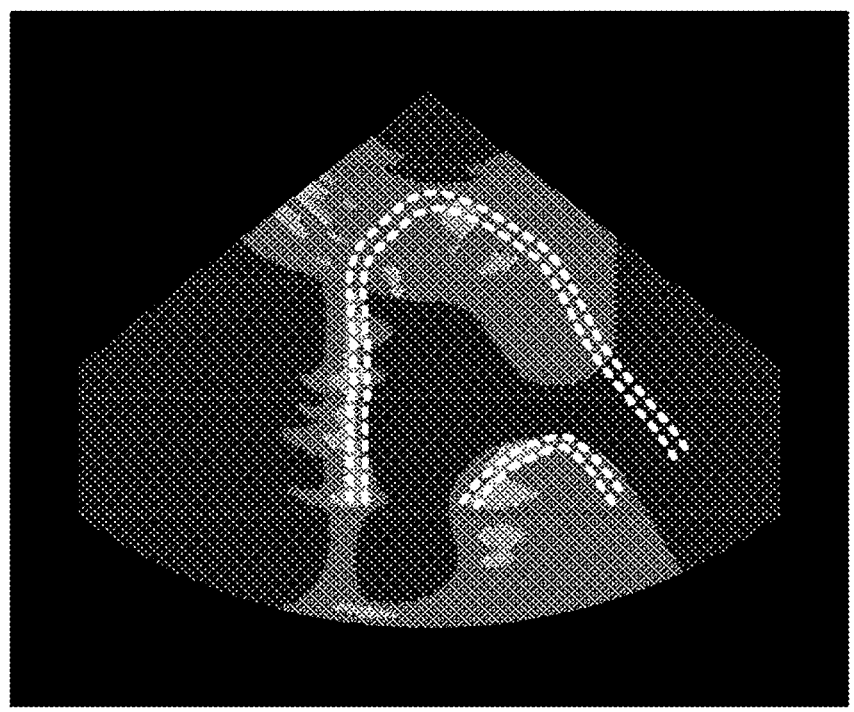
Figure 5:
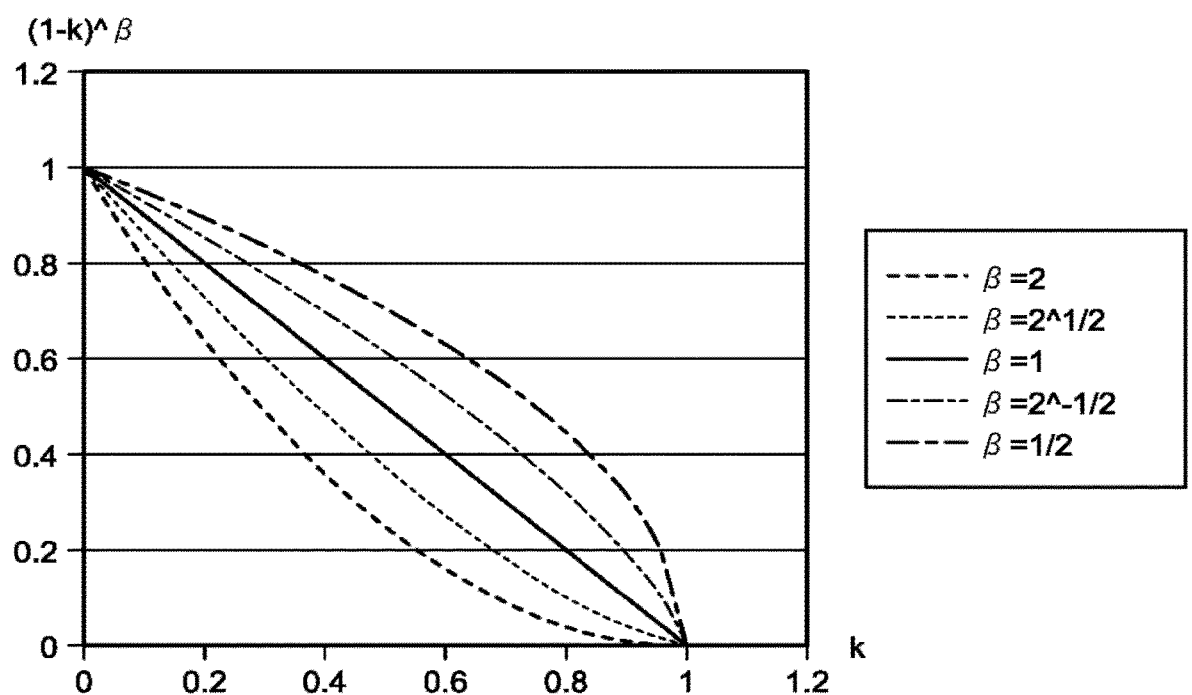
FIG. 5 is another drawing for explaining the process performed by the estimating function according to the first embodiment.

FIGS. 4A, 4E, and 5 are drawings for explaining processes performed by the estimating function 172 according to the first embodiment. FIG. 4A illustrates a correcting process performed on the initial contour (VI in FIG. 2) of the right ventricular endocardium. FIG. 4B illustrates a right ventricular (RV) coronal view. FIG. 5 illustrates an example of a characteristic with which corrected motion amounts are variably controlled by the estimating function 172.

At first with FIG. 4A, an example will be explained in which, among all the constituent points included in the contour of the right ventricular outflow tract, motion information of a point PV_in is corrected by using motion information of the crista supraventricularis (CSV), and subsequently, other points are corrected. The point PV_in is the constituent point positioned closest to the right ventricular outflow tract among the points on the circumference of the inner contour of the right ventricle corresponding to the pulmonary valve level. In the following sections, the point PV_in subject to the correction may also be referred to as a "first site", whereas a constituent point of the crista supraventricularis (CSV) to be used for the correction may also be referred to as a "second site". Further, original motion information at the point PV_in will be expressed as "V1", whereas original motion information in a position Pcsv of the crista supraventricularis will be expressed as "V2". In this situation, the original motion information denotes the motion information estimated in the WMT process described above. The letter "V" denotes a three-dimensional vector. The motion information in the first embodiment denotes a three-dimensional motion vector. Further, in the following sections, the absolute value of a vector X will be expressed as |X|.

In this situation, V2 additionally has a translation component of the entire heart, besides a contraction component of the myocardium at the crista supraventricularis. For this reason, the estimating function 172 obtains motion information "V2m" contributing to the systole of the crista supraventricularis after eliminating the translation component, so as to use "V2m" for the motion correction for the point PV_in. For this purpose, the estimating function 172 calculates an inter-frame rate of change LSR(N) in the length |L(N)| between a point Pa at the right ventricular apex and the crista supraventricularis. In this situation, LSR(N) can be expressed by using Expression (1) presented below.

$$LSR(N)=(|L(N+1)|-|L(N)|)/|L(N)| \qquad (1)$$

In this situation, the translation of the entire heart is considered to be substantially equal at the point Pa and at the crista supraventricularis. Accordingly, as indicated by the numerator of Expression (1), the translation component is cancelled out by calculating the vector difference between L(N+1) and L(N). Further, because the change in the length of |L(N)|*LSR(N) is defined by the orientation of the line segment connecting the point Pa to the point Pcsv of the crista supraventricularis, V2m can be expressed by using Expression (2) below, while using position vectors of these two points. In the right side of Expression (2), the term in the former half "Pcsv(N+1)−Pa(N+1)" expresses the vector defining the length "|L(N+1)|". The term in the latter half "Pcsv(N)−Pa(N)" expresses the vector defining the length "|L(N)|".

$$V2m=(Pcsv(N+1)-Pa(N+1))-(Pcsv(N)-Pa(N)) \qquad (2)$$

Because the difference in the position vector of each of the points between the frames corresponds to the motion of the point, when the motion information of the right ventricular apex is expressed as "V_PA", Expression (2) above can be expressed by using Expression (3) presented below. From Expression (3), it is understood that V2m includes the motion information "V2" of the crista supraventricularis.

$$V2m=V2-V\_PA \qquad (3)$$

Next, motion information "V1m" is obtained, which takes into account the contraction component at the point PV_in. In this situation, because the right ventricular outflow tract is an outflow tract of the blood flow, the primary contraction component is considered to be a component parallel to the direction of the blood flow. In the contour position of the point PV_in illustrated in FIG. 4A, the component parallel to the direction of the blood flow corresponds to the axial direction of the tract that is perpendicular to a cross-sectional plane of the tract (a cross-sectional plane in the direction orthogonal to the contour of the right ventricular outflow tract). It is possible to calculate the axial direction of the tract as, for example, a unit normal vector Nt_PV of a regression plane defined by using a group of contour boundary positions in a ring formation corresponding to a cross-sectional plane of the contour on the pulmonary valve level.

When Nt_PV is used as a direction component of the point PV_in, because V1m is a projection component of the original motion into this direction, V1m can be defined by using Expression (4) presented below. In the following sections, <u1,u2> denotes the inner product of vectors u1 and u2. The value of V1m calculated in this manner corresponds to motion information Vo' resulting from a component separation at the point PV_in (Vo'=V1m).

$$V1m = \langle V1, Nt\_PV \rangle * V1 \quad (4)$$

Similarly, the direction vector Nt_CSV of the component parallel to the direction of the blood flow with respect to the motion at the crista supraventricularis is considered to be the axial direction of the tract of the right ventricular outflow tract going through the crista supraventricularis. Accordingly, similarly to the example of the point PV_in, it is possible to calculate Nt_CSV as a unit normal vector of a regression plane defined by using a group of contour positions in a ring formation corresponding to a cross-sectional plane (among the directions orthogonal to the contour of the right ventricular outflow tract corresponding to anterior-wall-side hinge illustrated in FIG. 4A, the plane that goes through the crista supraventricularis) of the crista supraventricularis at the point Pcsv.

Possible methods for calculating the axial direction of the tract are not limited to the method described above. For example, while taking the moving direction the blood flow into consideration, it is also acceptable to calculate the axial direction of the tract as a unit direction vector extending from the right ventricular apex Pa toward a position PG of the center of gravity of the group of contour boundary positions in the ring formation corresponding to the cross-sectional plane in question.

In the present example, V2m includes the direction component other than the blood flow direction. Accordingly, a motion component V2mp that is parallel to the blood flow direction at the crista supraventricularis and contributes to the systole can be defined by using Expression (5) presented below while using Nt_CSV.

$$V2mp = \langle V2m, Nt\_CSV \rangle * V2m \quad (5)$$

By performing the component separation in the blood flow direction in this manner, with respect to the point PV_in and the point Pcsv of which the motion directions are not necessarily the same as each other because the positions thereof and the contour directions are different from each other, it is possible to compare and calculate the effective components with each other, the effective components being obtained by arranging the motion directions to be the same as each other.

Next, we will discuss how to transfer the motion information V2mp estimated at the point Pcsv as described above to the point. PV_in that is positioned apart therefrom.

In this situation, to perform a commonly-used one-dimensional interpolating process, values are given in the positions at two ends, so that an interpolation value in an arbitrary calculation position between the two ends is interpolated on the basis of both f the values in the positions at the two ends. However, in the first embodiment, a value is given only at one of the two end points. For this reason, to perform an interpolating process while no value given at the other end point, it is necessary to define an interpolation value in the calculation position. This process will be referred to as an "extrapolation process" in the first embodiment.

To perform the extrapolation process, it is defined that "the contraction component based on a rate of change in the length obtained from the crista supraventricularis is equal to the contraction component at the point PV_in". Accordingly, it is possible to estimate motion information of the point PV_in on the assumption that the rate of change "LSR(N)" in the length |L(N)| connecting the right ventricular apex to the crista supraventricularis is equal to the rate of change "L1SR(N)" in the length |L1(N)| of the line segment connecting the crista supraventricularis to the point PV_in. In this situation, when the motion to be observed at the point PV_in is expressed as V12m, it is possible to define V12m by using Expression (6) presented below while using the position vectors of the points.

$$V12m(PV\_\text{in}(N+1) - Pcsv(N+1)) - (PV\_\text{in}(N) - Pcsv(N)) \quad (6)$$

In Expression (6), the position Pcsv(N) of the crista supraventricularis before the move, the position Pcsv(N+1) of the crista supraventricularis after the move, and the position PV_(N) of the point PV_in before the move are known; however, the position PV_in(N+1) of the point PV_in after the move is unknown.

Because the difference in the position vector of each of the points between the frames indicates the motion, when the motion information of the point PV_in is expressed as "V_PV_in", Expression (6) above can be expressed by using Expression (7) presented below. It is understood from Expression (7) that V12m includes the motion information V2 of the crista supraventricularis. Further, as explained above, because the translation component is considered to be substantially equal at the crista supraventricularis and at the point PV_in, the translation component is cancelled out from V12m as a result of the difference calculating process between the two points.

$$V12m = V\_PV\_\text{in} - V2 \quad (7)$$

Next, the unknown position PV_in(N+1) will be determined for the purpose of calculating V12m. In this situation, because of the assumption that LSR(N) is equal to L1SR(N), Expression (8) presented below is satisfied.

$$LSR(N) = L1SR(N) = (|L1(N+1)| - |L1(N)|) / |L1(N)| \quad (8)$$

Further, from Expression (8), Expression (9) presented below is satisfied.

$$(LSR(N)+1) * |L1(N)| = |L1(N+1)| \quad (9)$$

In this situation, it is possible to express L1(N) and L1(N+1) by using Expressions (10) and (11) presented below.

$$L1(N) = (PV\_\text{in}(N) - Pcsv(N)) \quad (10)$$

$$L1(N+1) = PV\_\text{in}(N+1) - Pcsv(N+1) \quad (11)$$

Accordingly, PV_in(N+1) can be calculated by using Expression (12) presented below.

$$PV\_\text{in}(N+1) = (LSR(N)+1) * L1(N) + Pcsv(N+1) \quad (12)$$

By assigning PV_in (N+1) to Expression (7) above, V12 is calculated. Further, the motion component V12mp resulting from a component separation in the blood flow direction can be expressed by using Expression (13) presented below while using the direction vector Nt_PV at the point PV_in. The value of V12mp obtained in this manner corresponds to corrected motion information Vs' transferred from the crista supraventricularis to the point PV_in (Vs'=V12mp).

$$V12mp = \langle V12m, Nt\_PV \rangle * V12m \quad (13)$$

As explained above, as the motion information of the point PV_in resulting from the component separation in the blood flow direction, the two pieces of motion information, namely Vo' and Vs'(V12mp), are obtained. In this situation, considering the situation where |Vo'| of the point PV_in is decreased starting from the state where |Vo'| is larger than |Vs'| of the crista supraventricularis, no correction will be made when |Vo'| is sufficiently large, because it is considered that proper motion is obtained at the point PV_in. In contrast, when |Vo'| becomes smaller than |Vs'| because it is considered that proper motion is not obtained at the point PV_in, the correction amount shall be adjusted.

In other words, in the first embodiment, corrected motion information Vc is determined by comparing the motion amount |Vo'| of the point PV_in with the motion amount |Vs'| of the crista supraventricularis Pcsv. For example, the corrected motion information Vc is calculated by using Expression (14) presented below.

$$Vc = \begin{cases} Vs' - Vo' & (\text{when } |Vs'| \geq |Vo'|) \\ 0 & (\text{when } |Vs'| < |Vo'|) \end{cases} \quad (14)$$

In Expression (14), the value of |Vc| increases, as the value of |Vo'| becomes smaller relative to |Vs'|. When |Vo'| eventually becomes zero, Vc=Vs' is satisfied, and |Vc|=|Vs'| is therefore satisfied. When a motion correction is made on the point PV_in by using Expression (14), the motion correction means that the motion of the point PV_in is replaced with Vs' regardless of the motion Vo' of the point PV_in, except for the component separation with the main direction (corresponding to the situation where Nt_PV is considered to be oriented in the exactly same direction as V1).

Further, in place of Expression (14), it is also possible to calculate corrected motion information Vc by using Expression (15) presented below.

$$Vc = \begin{cases} ((|Vs'| - |Vo'|)/|Vs'|)^\beta * Vs' & (\text{when } |Vs'| \geq |Vo'|) \\ 0 & (\text{when } |Vs'| < |Vo'|) \end{cases} \quad (15)$$

In Expression (15), when "1" is assigned to "β" in the exponential term, the output changes while |Vs'|≥|Vo'| is satisfied can be expressed by using Expression (16) presented below. In other words, when Expression (15) is used, similarly to the situation where Expression (14) is used, the value of |Vc| increases as the value of |Vo'| becomes smaller relative to |Vs'|, and when |Vo'| eventually becomes zero, Vc=Vs' is satisfied, and |Vc|=|Vs'| is therefore satisfied.

$$Vc = Vs'*(1 - |Vo'|/|Vs'|) \quad (16)$$

In this situation, we put "k=|Vo'|/|Vs'|", which is assigned to Expression (16) presented above corresponding to when |Vs'|≥|Vo'| is satisfied, then Expression (16) can be rearranged into Expression (17) presented below.

$$Vc = Vs'*(1-k)^\beta \quad (17)$$

With regard to the variable term "$(1-k)^\beta$" in Expression (17) above, FIG. 5 illustrates the manner in which the value changes depending on k, while the value of β is varied. In FIG. 5, the horizontal axis expresses "k", whereas the vertical axis expresses the variable term "$(1-k)^\beta$".

As illustrated in FIG. 5, the value of the variable term decreases, as the value of k increases. Conversely, when k decreases from 1, the variable term, which corresponds to the corrected motion amount, increases. In particular, when "β=1" is satisfied, the value of the variable term changes in the manner of a linear function (linearly), as the value of k changes. Further, it is observed that when "β>1" is satisfied, the corrected motion amount is smaller than that during the linear change. It is also observed that when "β<1" is satisfied, the corrected motion amount is larger than that during the linear change. Accordingly, freedom is granted where, when it is desired to obtain a motion correction controlled value that is relatively large in accordance with k, which is the ratio |Vo'|/|Vs'|, "β<1" can be selected; and when it is desired to obtain a motion correction controlled value that is relatively small in accordance with k, "β>1" can be selected.

As explained above, when the correction is made by using Expression (15), it is possible to adjust how much motion correction amount is to be applied as Vc, depending on the setting of β. In this situation, from the viewpoint of achieving a larger correction amount, it is desirable to set β to satisfy β=0.5 to 0.7 approximately.

Further, by using the corrected motion information Vc for the crista supraventricularis obtained from the processes described above, the point PV_in, which is subject to the correction, is moved from PV_in(N) to PV_in(N+1). In other words, in each of the frames used in the 3DWMT process, the original motion Vo at the point PV_in is replaced with Von calculated in Expression (18). In Expression (18), when "Vc={0} (where {0} denotes a zero vector)" is satisfied, Von=Vo is true, which is equivalent to making no corrections.

$$Von = Vo + Vc \quad (18)$$

With the processes described above, the corrected motion information Vc is obtained for the point PV_in, which is one point of the right ventricular outflow tract, and it is therefore possible to make the motion correction on the point PV_in. However, to move the entire ROI related to the right ventricular outflow tract, it is necessary to obtain the corrected motion information Vc for all the constituent points structuring the contour of the right ventricular outflow tract.

To cope with this situation, among all the constituent points structuring the contour of the right ventricular outflow tract, the estimating function 172 calculates corrected motion information Vc for a plurality of constituent points that are discretely positioned, by performing the extrapolation process described above. After that, by performing a spatial interpolation process while using the corrected motion information Vc of the plurality of discretely-positioned constituent points, the estimating function 172 calculates corrected motion information for all the constituent points of the right ventricular outflow tract. In this situation, as the interpolation process, it is desirable to perform a two-dimensional interpolating process by adopting, for example, a bi-linear interpolating process while using corrected motion information Vc of four-point positions closest to the interpolation position or a one-dimensional linear interpolating process while using corrected motion information Vc of two-point positions closest to the interpolation position in both the longitudinal direction and the circumferential direction of a boundary plane.

Alternatively, without using the interpolation process, it is also possible to calculate the corrected motion information Vc by using the extrapolation process described above for all the constituent points of the right ventricular outflow tract, for example. It should be noted, however, because the calculation time period required by the interpolation process is shorter than that required by the extrapolation process described above, it is preferable to calculate the corrected motion information for all the constituent points of the right ventricular outflow tract by using the interpolation process. In the following sections, an example will be explained in which the estimating function 172 calculates the corrected motion information for all the constituent points of the right ventricular outflow tract by using the interpolation process.

As illustrated in FIG. 4A, for example, the estimating function 172 calculates the corrected motion information Vc of each of three points PV_out. In this situation, the points PV_out are constituent points that are discretely arranged on a ring-shaped boundary plane on the pulmonary valve level and are different from the point PV_in.

In this situation, the point PV_in will be used as a new "second site", whereas the value Von described above obtained at the point PV_in will be used as a new piece of "motion information (V2) of the second site" at the second site. Because the value Vo at the point PV_in is equal to V_PV_in, "V2" in this situation can be expressed by using Expression (19) by using previously-obtained "Vc".

$$V2 = Von = V\_PV\_in + Vc \quad (19)$$

Further, by using each of the points "PV_out" as a new "first site", a new piece of corrected motion information Vc with respect to the original motion V_PV_out of the first site is calculated by performing the same process as the extrapolation process described above.

First, the estimating function 172 performs a component separation process in the blood flow direction. For example, because the direction vector at the second site (the point PV_in) is equal to Nt_PV, the motion information V2' obtained from the component separation on the value V2 above can be expressed by using Expression (20) presented below.

$$V2' = \langle V2, Nt\_PV \rangle * V2 \quad (20)$$

Subsequently, because the direction vector at each of the points PV_out is equal to Nt_PV similarly to that at the point PV_in, the value of Vo' resulting from a component separation in this position can be expressed by using Expression (21) presented below.

$$Vo' = \langle V\_PV\_out, Nt\_PV \rangle * V\_PV\_out \quad (21)$$

In this situation, the extrapolation process is based on the notion that "contraction motion components in the blood flow direction are equal to one another on the circumference on mutually-the-same right ventricular outflow tract level". In other words, V2' obtained as a direction component at each of the points PV_out for the motion information at the second site previously obtained at the point PV_in will be given as Vs' to a corresponding one of the points PV_out. In other words, Vs'=V2' is satisfied.

As a result, two pieces of motion information, namely Vo' and Vs', are obtained for each of the points PV_out. Accordingly, by using the expressions above as appropriate, the estimating function 172 calculates corrected motion information Vc1 of each of the points PV_out.

After that, the extrapolation process in the circumferential direction is similarly applicable to three points CSV_out illustrated in FIG. 4A on the ring-shaped boundary plane of the right ventricular outflow tract on the crista supraventricularis level. In other words, because the second site on the right ventricular outflow tract level is the crista supraventricularis, Vs' is given to each of the points CSV_out by using previously-obtained Vs'=V2mp.

Further, the original motion at each of the points CSV_out serving as the first site will be expressed as "V_CSV_out". In this situation, because the direction of the component separation is expressed as Nt_CSV, which was previously obtained, it is possible to calculate Vo' resulting from a component separation in this position by using Expression (22) presented below.

$$Vo' = \langle V\_CSV\_out, Nt\_CSV \rangle * V\_CSV\_out \quad (22)$$

As a result, two pieces of motion information, namely Vo' and Vs', are obtained for each of the points CSV_out. Consequently, by using the expressions above as appropriate, the estimating function 172 calculates the corrected motion information Vc2 of each of the points CSV_out.

In the first embodiment, because the corrected motion information is calculated for the discrete points of the right ventricular outflow tract, the corrected motion information is calculated as described above with respect to each of the points in the circumferential direction and the tract axial direction by using the interpolation processes. In one example, by performing the interpolation process that uses the pieces of corrected motion information of the point PV_in and the points PV_out, the estimating function 172 calculates the corrected motion information of each of the constituent points on the circumference on the pulmonary valve level. Further, by performing the interpolation process that uses the pieces of corrected motion information of the point Pcsv and the points CSV_out, the estimating function 172 calculates the corrected motion information of each of the constituent points on the circumference on the crista supraventricularis level. After that, by performing the interpolation process that uses the corrected motion information of each of the constituent points on the circumference on the pulmonary valve level and the corrected motion information of each of the constituent points on the circumference on the crista supraventricularis level, the estimating function 172 calculates the corrected motion information for each of the points in the tract axial direction.

As explained above, the estimating function 172 calculates the corrected motion information at each of all the constituent points of the right ventricular outflow tract. In this situation, from the viewpoint of reducing the noise that may occur at the time of the calculation of the corrected motion information, a preferable embodiment includes the process of obtaining corrected motion having a smooth distribution by applying a spatial smoothing process (preferably, a median filter process or a convolution average process performed on the two-dimensional space of the boundary plane mesh) to the distribution value of the corrected motion information on the boundary plane with respect to all the constituent points of the right ventricular outflow tract obtained as described above.

Figure 6A:
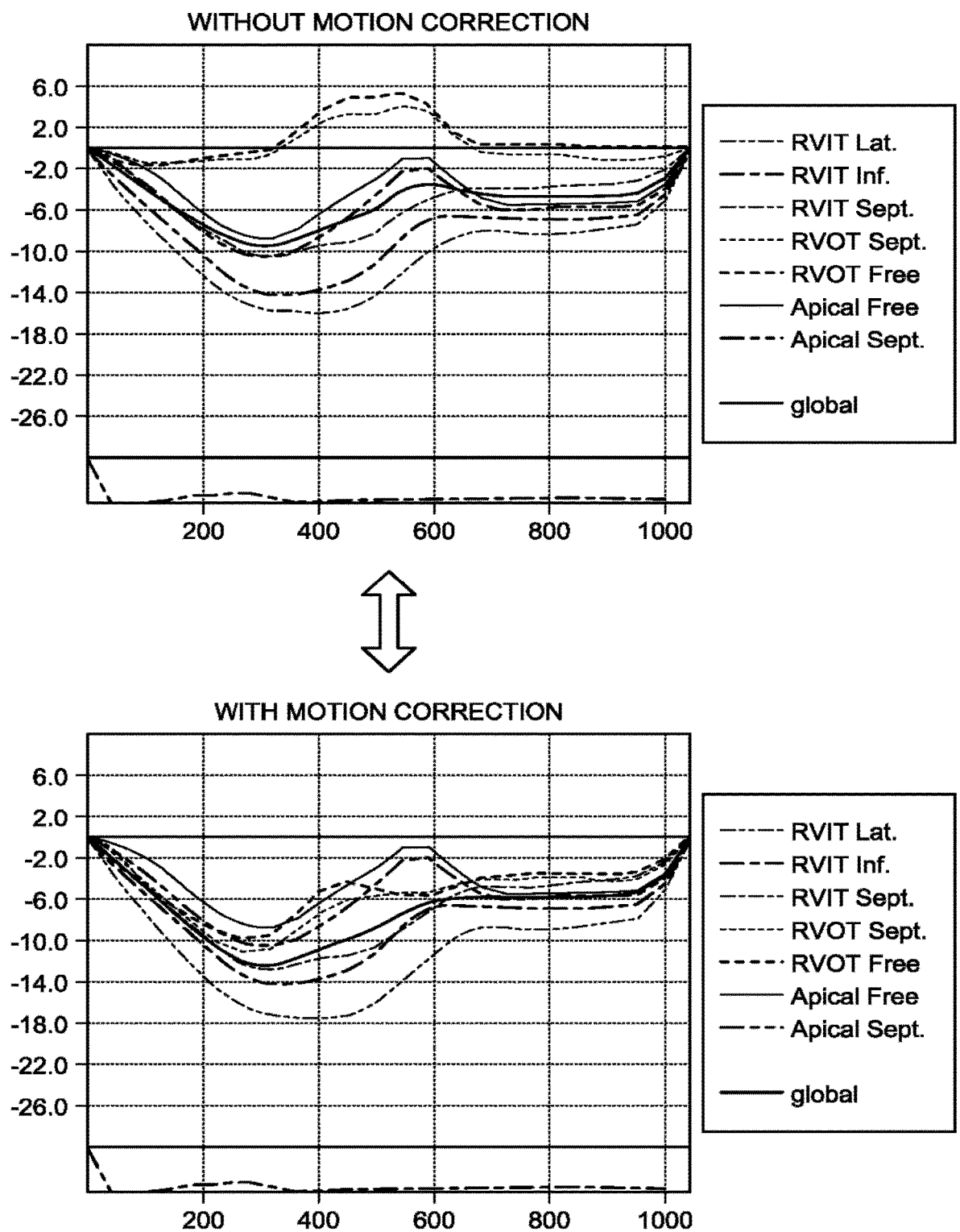
FIGS. 6A to 6C are drawings for explaining impacts of a motion correcting process performed by the estimating function according to the first embodiment.
Figure 6B:
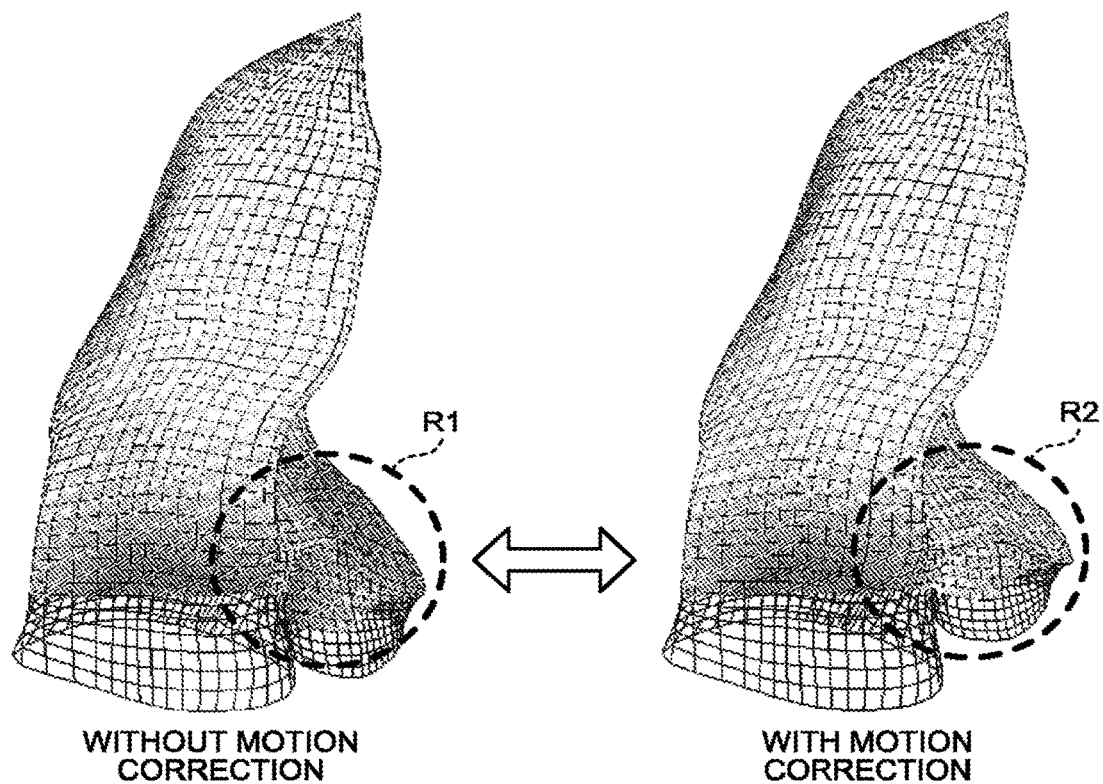
Figure 6C:
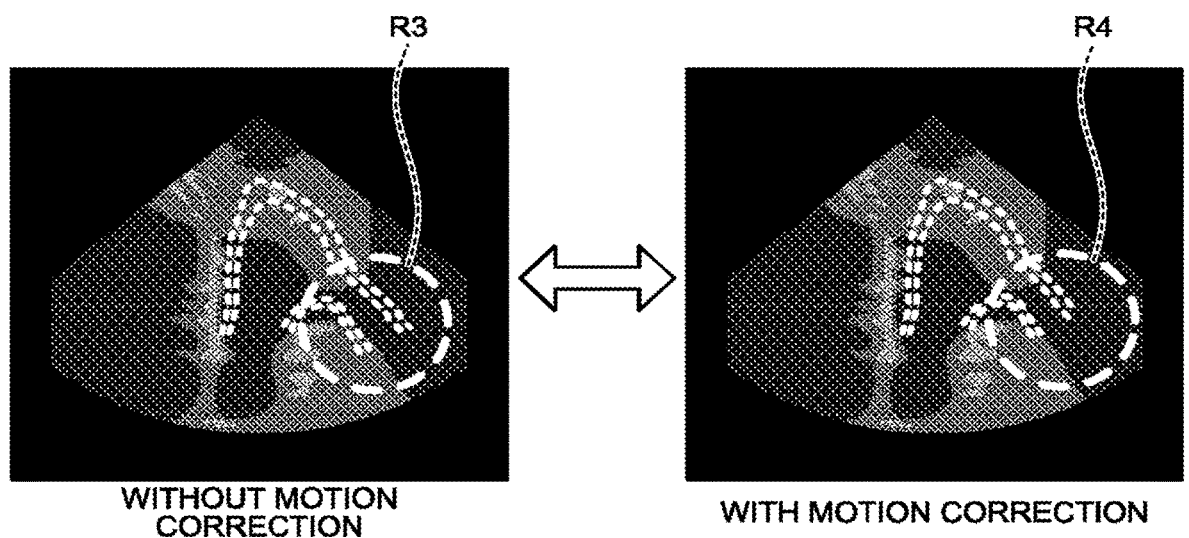

FIGS. 6A, 6B, and 6C are drawings for explaining impacts of the motion correcting process performed by the estimating function 172 according to the first embodiment. FIG. 6A presents charts illustrating changes in Longitudinal Strain (LS). FIG. 6B illustrates a display image in which color codes corresponding to the motion information (where darker colors are assigned to smaller values) are mapped over the contour of the right ventricular endocardium. FIG.

6C illustrates the position of the right ventricular contour in right ventricular (RV) coronal views.

As illustrated in FIGS. 6A to 6C, it is observed that, as a result of the motion correction (the correcting process) according to the first embodiment, the right ventricular outflow tract is arranged to have systolic movements, and the LS curves in the corresponding two segments ("RVOT Sept." and "RVOT Free" in FIG. 6A) are corrected. More specifically, in the situation without the motion correction, as illustrated in the region R1 of FIG. 6B, darker colors are assigned to the right ventricular outflow tract in comparison to other regions. This means that the motion information of the right ventricular outflow tract has a small value and is almost zero in the example illustrated in FIG. 6E. In other words, in the situation without the motion correction, it is observed that the right ventricular outflow tract hardly moves. For this reason, as illustrated in the region R3 of FIG. 6C, the right ventricular outflow tract is observed as locally extending in the lower right direction of the drawing (as if the right ventricular outflow tract were expanding). Further, in the chart on the top section of FIG. 6A, LS exhibits a positive value in the end-systolic phase. In contrast, in the situation with the motion correction, as illustrated in the region R2 of FIG. 6B, because lighter colors are assigned to the right ventricular outflow tract in comparison to the region R1, it is observed that motion information of the right ventricular outflow tract is obtained. For this reason, the extending of the site in the lower right direction illustrated in the region R3 of FIG. 6C is resolved, so that the contraction of the right ventricular outflow tract can be observed as illustrated in the region R4 of FIG. 6C. Also, in the chart in the bottom section of FIG. 6A, it is observed that the curve of LS of the right ventricular outflow tract is improved.

Figure 7:
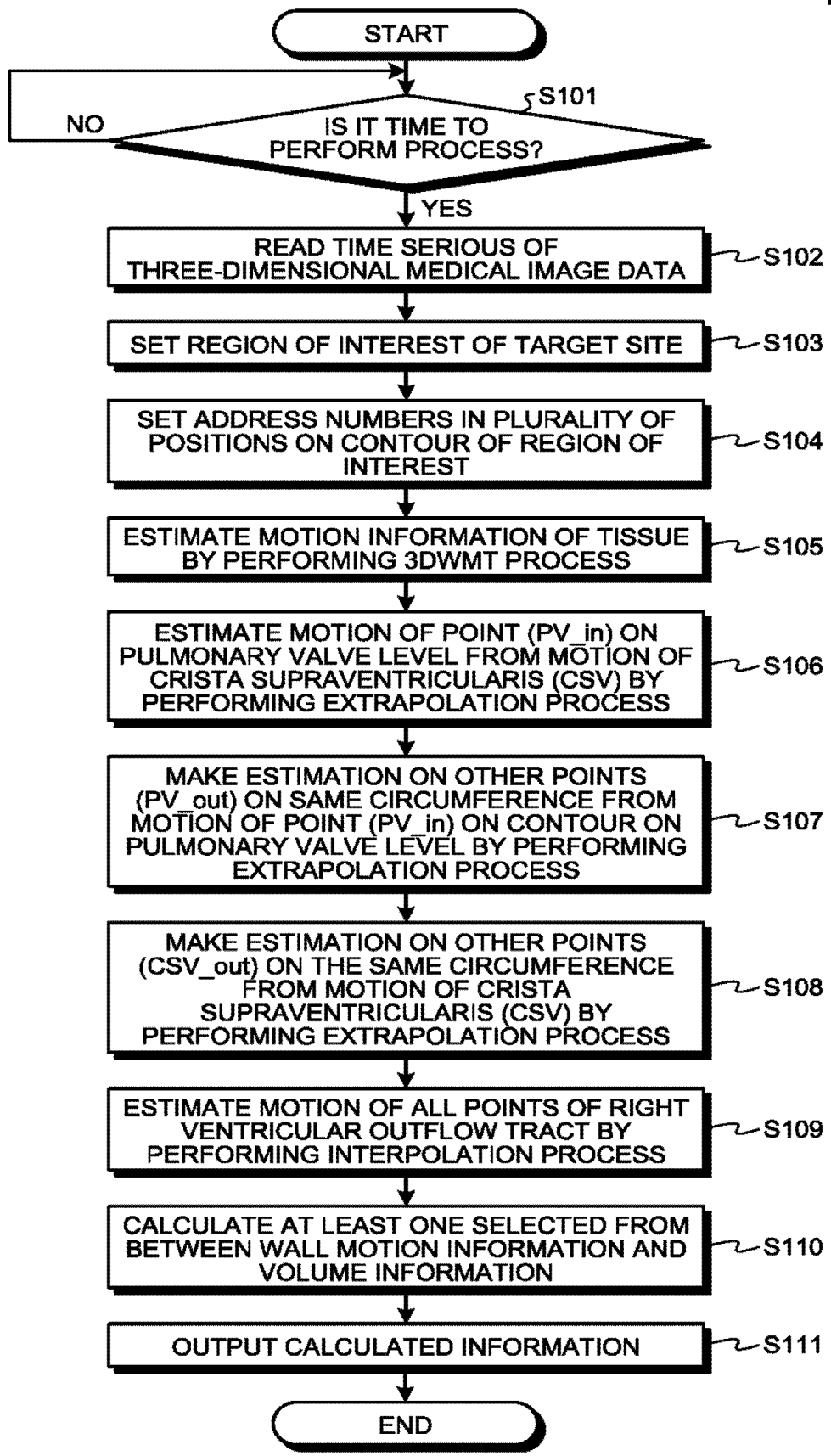
FIG. 7 is a flowchart illustrating a processing procedure performed by the ultrasound diagnosis apparatus according to the first embodiment.

FIG. 7 is a flowchart illustrating a processing procedure performed by the ultrasound diagnosis apparatus 1 according to the first embodiment. The processing procedure illustrated in FIG. 7 is started, for example, when an instruction is received from the operator indicating that a wall motion tracking process is to be started.

At step S101, it is judged whether it is time to perform the process. For example, the input device 102 receives an instruction from the operator indicating that a wall motion tracking process is to be started, and sends the received instruction to the processing circuitry 170. When having received the instruction transferred thereto by the input device 102, the processing circuitry 170 determines that it is time to perform the process (step S101: Yes) and starts the processes at step S102 and thereafter. When it is not time to perform the process (step S101: No), the processes at step S102 and thereafter will not be started, and the processing functions of the processing circuitry 170 remain in a standby state.

When the judgment result at step S101 in the affirmative, the obtaining function 171 reads three-dimensional medical image data (volume data) at step S102. For example, the obtaining function 171 reads, from the image memory 150, a group of volume data corresponding to at least one cardiac cycle and being taken of a region including the right ventricle of the patient P.

At step S103, the estimating function 172 sets a region of interest of the target site. For example, by applying a segmentation process to the volume data, the estimating function 172 detects a region corresponding to the right ventricle. After that, the estimating function 172 sets an initial contour with the detected region.

At step S104, the estimating function 172 sets address numbers with a plurality of positions on the contour of the region of interest. For example, the estimating function 172 sets a plurality of tracking points (constituent points) to which the address numbers have been assigned, with positions corresponding to the contour of the right ventricle, in at least one of the pieces of volume data included in the group of volume data.

At step S105, the estimating function 172 estimates motion information of the tissue by performing a 3DWMT process. For example, by performing a tracking process including a pattern matching process while using the volume data in an initial temporal phase in which the plurality of constituent points were set and the volume data in the subsequent temporal phase, the estimating function 172 tracks the positions of the plurality of constituent points in the plurality of pieces of ultrasound image data included in the group of volume data.

At step S106, the estimating function 172 estimates motion of the point (PV_in) on the pulmonary valve level, on the basis of motion of the crista supraventricularis (CSV), by performing an extrapolation process. For example, the estimating function 112 calculates corrected motion information of the point PV_in by using motion information of the crista supraventricularis, based on the definition that "the contraction component based on a rate of change in the length obtained from the crista supraventricularis is equal to the contraction component at the point PV_in".

At step S107, the estimating function 172 makes estimation on other points (PV_out) on the same circumference, on the basis of the motion of the point (PV_in) on the contour on the pulmonary valve level, by performing an extrapolation process. For example, the estimating function 172 calculates corrected motion information of the points PV_out by using the motion information of the point PV_in, on the basis of the definition that "contraction motion components in the blood flow direction are equal to one another on the circumference on mutually-the-same right ventricular outflow tract level".

At step S108, the estimating function 172 makes estimation on other points (CSV_out) on the same circumference on the basis of the motion of the crista supraventricularis (CSV) by performing an extrapolation process. For example, the estimating function 172 calculates corrected motion information of the points CSV_out by using the motion information of the crista supraventricularis, on the basis of the definition that "contraction motion components in the blood flow direction are equal to one another on the circumference on mutually-the-same crista supraventricularis level".

At step S109, the estimating function 172 estimates motion of all the points of the right ventricular outflow tract, by performing an interpolation process. For example, the estimating function 172 calculates corrected motion information for each of the points in the tract axial direction, by performing an interpolation process while using corrected motion information of the constituent points on the circumference on the pulmonary valve level and corrected motion information of the constituent points on the circumference on the crista supraventricularis level.

At step S110, the calculating function 173 calculates at least one selected from between wall motion information and volume information. For example, the calculating function 173 calculates a local myocardial displacement [mm] of each of the constituent points in each frame, a local myocardial strain value [%] indicating a rate of change in the distance between two points, or a temporal change in either of these values such as a local myocardial velocity value [cm/s] or a local myocardial strain rate [1/s], for example.

At step S111, the output controlling function 174 outputs the calculated information. For example, the output controlling function 174 converts either the wall motion information or the volume information calculated by the calculating function 173 into color codes and further maps the color codes over a display image. Further, for example, the output controlling function 174 calculates an average value for each of the segments included in the region of interest, by using the wall motion information calculated for each of the constituent points. After that, the output controlling function 174 generates and displays a time-change curve with respect to the calculated average values. Subsequently, the processing circuitry 170 ends the process.

As explained above, the processing circuitry 170 performs the 3DWMT process on the right ventricle, including the correcting process on the right ventricular outflow tract. The processing procedure illustrated in FIG. 7 is merely an example, and possible embodiments are not limited to the processing procedure in the drawing. For instance, as for the processes at step S107 and step S108, either one of the processes may be performed first.

In the processing procedure illustrated in FIG. 7, the example is explained in which, with respect to the tract axial direction of the right ventricular outflow tract, the positions between the constituent points on the circumference at the upper end (on the crista supraventricularis level) and the constituent points on the circumference at the lower end (on the pulmonary valve level) are calculated by performing the interpolation process; however, possible embodiments are not limited to this example. For instance, the estimating function 172 may calculate constituent points on circumferences on a number of position levels in the tract axial direction of the right ventricular outflow tract by performing an extrapolation process and subsequently perform an interpolation process in the tract axial direction. By increasing, in this manner, the number of position levels on which the calculation is performed through the extrapolation processes in the tract axial direction, it is possible to improve the level of precision of the corrections in the tract axial direction.

As explained above, in the ultrasound diagnosis apparatus 1 according to the first embodiment, the estimating function 172 is configured to correct the first motion information of the right ventricular outflow tract by using the second motion information of the site that is positioned in the vicinity of the right ventricular outflow tract and exhibits motion similar to that of the right ventricular outflow tract. With this arrangement, the ultrasound diagnosis apparatus 1 according to the first embodiment is able to improve the quality of the analyses of the motion (the motion tracking) of the right ventricular outflow tract. In other words, even when it is difficult to observe the right ventricular outflow tract, as long as it is possible to obtain, from at least one point, the motion information of the site that is positioned in the vicinity of the right ventricular outflow tract and exhibits motion similar to that of the right ventricular outflow tract, the ultrasound diagnosis apparatus 1 is able to obtain the motion information of all the points of the right ventricular outflow tract, by using the obtained motion information. Accordingly, when the 3DWMT process is performed on the right ventricle by using three-dimensional video data obtained from a body-surface ultrasound probe, it is possible to improve the quality of the analyses of the motion (the motion tracking) of the right ventricular outflow tract.

Further, for example, the estimating function 172 is configured to correct the motion information that is a part of the first motion information and is related to the component in the contour direction of the tissue parallel to the blood flow direction, by using the motion information that is a part of the second motion information and is related to the component in the contour direction (the tract axial direction) of the tissue parallel to the blood flow direction. More specifically, with respect to the first motion information, the motion information related to either the component in the blood flow direction at the first site or the component in the contour direction of the tissue at the first site parallel to the blood flow direction at the first site is used. Further, with respect to the second motion information, the motion information related to either the component in the blood flow direction at the first or the second site or the component in the contour direction of the tissue at the first or the second site parallel to the blood flow direction at the first or the second site is used (where the choice from between the first site and the second site should match throughout the procedure). As a result, the estimating function 172 is able to estimate the motion information in the systolic direction of the right ventricular outflow tract, by using the motion information including the direction components other than the systolic direction of the right ventricular outflow tract.

Further, for example, the estimating function 172 is configured to correct the first motion information by using the spatial extrapolation process. In one example, by performing the extrapolation process, the estimating function 172 estimates the motion of the point PV_in on the pulmonary valve level on the basis of the motion of the crista supraventricularis. As a result, the estimating function 172 is able to estimate the motion information of the unknown point, by using the motion information of the single known point.

Further, for example, the estimating function 172 is configured to calculate the corrected motion information used for correcting the first motion information, by comparing the first motion information with the second motion information. In one example, by using either Expression (14) or Expression (15), the estimating function 172 calculates the corrected motion information Vc. As a result, the estimating function 172 is able to make an appropriate correction depending on whether the first motion information is sufficiently obtained or not.

Further, for example, the estimating function 172 is configured to add the corrected motion information to the first motion information. More specifically, the estimating function 172 adds, as indicated in Expression (18), the corrected motion information Vc to the original motion information Vo at the point PV_in. As a result, by using the original motion subject to the correction, the estimating function 172 is able to make a correction so that the motion component of the tissue perpendicular to the blood flow direction remains.

Further, for example, when the second site is the crista supraventricularis, the estimating function 172 is configured to calculate third motion information of the single point of the right ventricular outflow tract on the pulmonary valve level by performing the extrapolation process while using the second motion information and to further calculate fourth motion information of other points of the right ventricular outflow tract on the circumference on the pulmonary valve level by performing the extrapolation process while using the calculated third motion information. In one example, on the basis of the motion of the point PV_in on the contour on the pulmonary valve level, the estimating function 172 makes the estimation on the other points PV_out on the same circumference, by performing the extrapolation process. As a result, the estimating function 172 is able to make the corrections with respect to the unknown points, which could not be corrected by the interpolation process using the known points.

Further, for example, the estimating function 172 is configured to calculate the second motion information by using at least one selected from between the rate of change in the length between the cardiac apex of the right ventricle and the second side and the rate of change in the length between the second site and a point that is positioned in the vicinity of the second site and is in the direction substantially parallel to the right ventricular outflow tract. For example, as illustrated in the numerator of Expression (1), the estimating function 172 calculates the difference between L(N+1) and L(N). As a result, the estimating function 172 is able to make the correction after cancelling out the translation component.

Further, for example, the estimating function 172 is configured to compare the magnitude of the first motion information with the magnitude of the second motion information and, when the magnitude of the first motion information is larger, the estimating function 172 arranges the corrected motion information to be zero, and when the magnitude of the first motion information is smaller, the estimating function 172 adjusts the corrected motion information in accordance with the degree of the magnitude of the first motion information relative to the magnitude of the second motion information. In one example, the estimating function 172 calculates the corrected motion information Vc by using either Expression (14) or Expression (15). As a result, the estimating function 172 is able to adjust the corrected motion information (the corrected motion amount) used in the correcting process, in accordance with the degree of the obtained first motion information.

Second Embodiment

In the first embodiment, the example is explained in which the ultrasound diagnosis apparatus 1 uses the constituent points of the crista supraventricularis as the "second site". However, possible embodiments are not limited to this example. For instance, besides the crista supraventricularis, the aortic valve (AV) may be used as a site that is positioned in the vicinity of the right ventricular outflow tract and exhibits motion similar that of the right ventricular outflow tract.

Figure 8:
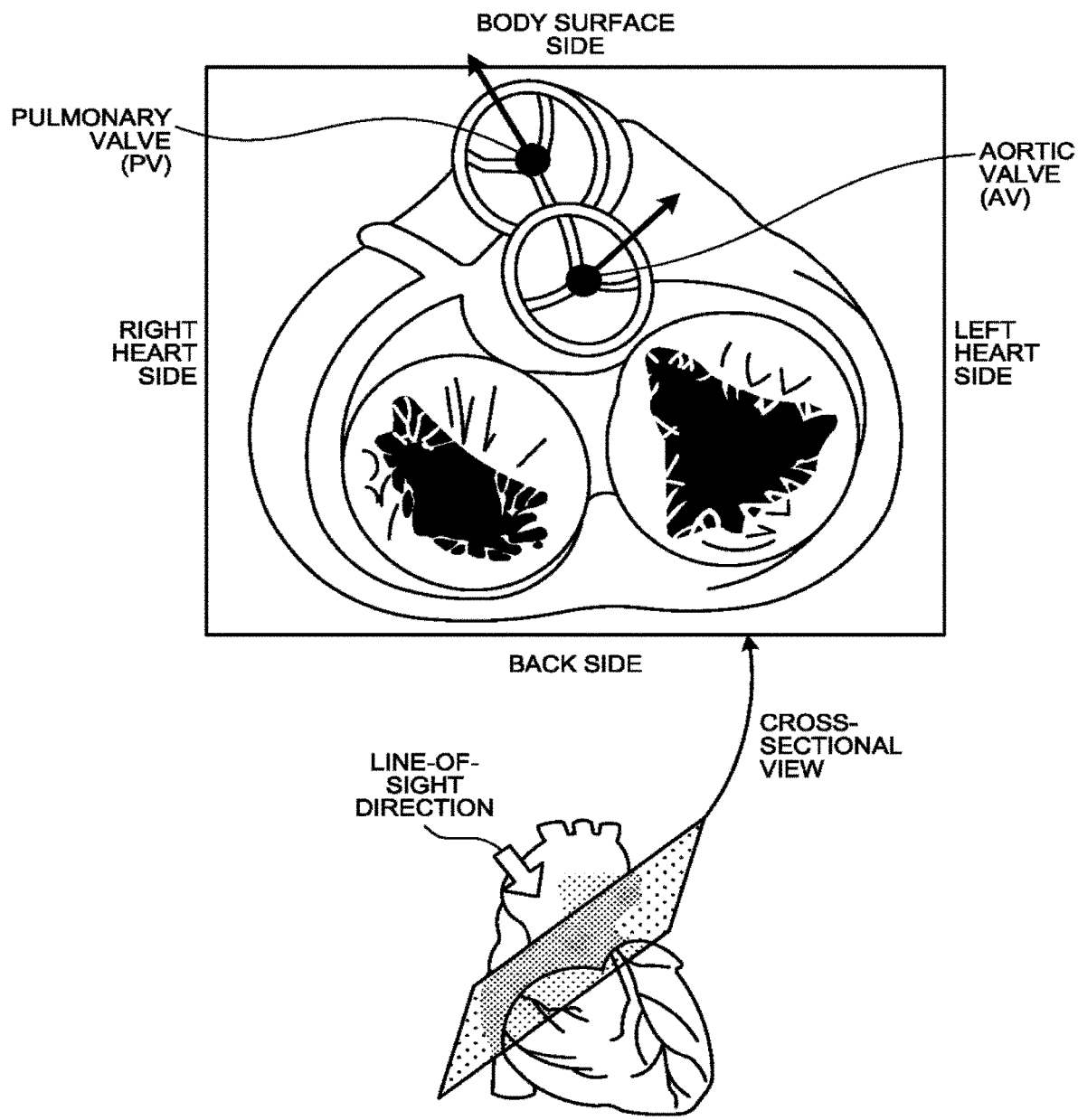
FIG. 8 is a drawing illustrating a positional relationship between the pulmonary valve and the aortic valve.

FIG. 8 is a drawing illustrating a positional relationship between the pulmonary valve and the aortic valve. The top section of FIG. 8 illustrates a cross-sectional view of the heart illustrated in the bottom section of FIG. 8. The cross-sectional view in the top section of FIG. 8 is a cross-sectional view taken in the line-of-sight direction indicated with the arrow in the bottom section of FIG. 8 (i.e., a view from the head side of the patient). In the top section of FIG. 8, the top of the drawing corresponds to the body surface side (the abdomen side) of the patient P, the bottom of the drawing corresponds to the back side of the patient P, the right of the drawing corresponds to the left heart side of the patient P, and the left of the drawing corresponds to the right heart side of the patient P.

As illustrated in FIG. 8, the aortic valve is positioned substantially in the vicinity of the pulmonary valve in the heart of the patient P. As for the aortic valve and the pulmonary valve, the annuli of the two valves move in the blood vessel direction in conjunction with pulsation of the heart. More specifically, in the systolic period, the left heart and the right heart both contract so as to pump out the same volume of blood flow to the aorta and to the pulmonary artery, and at which time the two annuli each move toward the blood vessel thereof (the aorta and the pulmonary artery). In contrast, during the diastolic period, as the left heart and the right heart expand, both of the annuli return to the positions observed at the beginning of the contraction. As a result, the motion amount of the annulus of the pulmonary valve is considered to be substantially correlated with the degree of the motion amount of the annulus of the aortic valve. In this situation, although it is difficult to acquire echo signals from the annulus of the pulmonary valve because the sternum is positioned nearby, it is easier to acquire echo signals from the annulus of the aortic valve because the blood in the right ventricular outflow tract and the pulmonary artery and the blood in the cardiac lumen in the surroundings allow ultrasound waves to pass. Thus, in a second embodiment, an example will be explained in which the aortic valve is used as the second site.

The ultrasound diagnosis apparatus 1 according to the second embodiment has the same configuration as that of the ultrasound diagnosis apparatus 1 illustrated in FIG. 1, except that a part of the processes performed by the estimating function 172 is different. The second embodiment will therefore be explained while a focus is placed on the differences from the first embodiment. The explanation of come of the element having the same functions as those in the first embodiment will be omitted.

As for the ROI in the right ventricle, the motion information thereof including that of the annulus site of the pulmonary valve in the right ventricular outflow tract has been obtained through the 3DWMT process. Further, in the second embodiment, it is necessary to obtain motion of the annulus site of the aortic valve. Thus, the estimating function 172 according to the second embodiment further performs a segmentation process on the annulus site of the aortic valve and a tracking process on the annulus site of the aortic valve.

In this situation, to perform the segmentation process on the annulus site of the aortic valve, an initial position of the annulus site of the aortic valve in an initial temporal phase is obtained by implementing either a first setting method or a second setting method described below. The first setting method is a method by which the position of the annulus site of the aortic valve is automatically detected as the initial position, by comparing a shape database of the annulus site of the aortic valve created through a machine-learning process or the like with three-dimensional image data that is input. The second setting method is a method by which the position of the annulus site of the aortic valve is set as the initial position by having the operator designate a position (through a manual tracing process, or the like) within the display of an MPR image corresponding to three-dimensional image data that is input.

Further, to perform the tracking process on the annulus site of the aortic valve, motion of the position of the annulus site of the aortic valve between temporal phases is obtained by a three-dimensional speckle tracking process including a template matching process, so as to track the position of the annulus site of the aortic valve with respect to all the temporal phases.

In the second embodiment, the center of gravity of the position of the ring-shaped boundary plane of the annulus site of the aortic valve is used as the "second site", whereas each of the constituent points in the circumferential direction of the annulus site of the pulmonary valve (corresponding to the position of the ring-shaped boundary plane on the pulmonary valve level in the first embodiment) is used as the "first site". Further, the original motion Vo2 at the second site is calculated by using the inter-frame difference between the position vectors of the center of gravity, whereas the original motion at the first site is expressed as Vo1.

In this situation, as explained in the first embodiment, a pre-processing process may be performed to eliminate the translation component. In that situation, V2 and V1 are obtained as motion values after the translation component is eliminated, by using motion information V_PA of the right ventricular apex described above for the first site and using motion V_PB of the left ventricular apex Pb, similarly to the right ventricular apex, for the second site. For example, V2 and V1 can be calculated by using Expressions (23) and (24) presented below.

$$V2 = Vo2 - V\_PB \quad (23)$$

$$V1 = Vo1 - V\_PA \quad (24)$$

Subsequently, the blood flow directions used for the component separation are the axial directions of the two blood vessels at the annulus sites, as indicated by the arrows in FIG. 8. For the blood flow direction at the annulus site of the pulmonary valve, Nt_PV obtained in the first embodiment shall be used. For the blood flow direction at the annulus site of the aortic valve, it is desirable, similarly to the pulmonary valve level, to calculate and use the unit normal vector Nt_AV of the regression plane defined in the ring-shaped contour position of a transversal cross-sectional plane of the aorta corresponding to the annulus site of the aortic valve.

Accordingly, motion information V2m of the second site and motion information V1m of the first site resulting from the component separation can be expressed respectively by using Expression (25) and Expression (26) presented below. In other words, as the second motion information, the estimating function 172 uses the motion information component in the blood vessel axial direction of the aorta with respect to the annulus site of the aortic valve.

$$V2m = \langle V2, Nt\_AV \rangle * V2 \quad (25)$$

$$V1m = \langle V2, Nt\_PV \rangle * V1 \quad (26)$$

In this situation, the extrapolation process uses the notion "the motion component amount |V1m| of the annulus site of the pulmonary valve is equal to the motion component amount |V2m| of the annulus site of the aortic valve". Further, it is assumed that this relationship is also true in each of the positions (the constituent points) in the circumferential direction on the annulus level of the pulmonary valve. As a result, as the two pieces of motion information Vo' and Vs', "Vo'=V1m" and "Vs'=|V2m|*Nt_PV" are obtained. The former expression is obvious from the definition. The latter expression indicates that, for the magnitude of the motion information to be transferred, the motion amount on the aortic valve side is used, and for the direction of the motion information, the direction is converted as a direction of the motion on the pulmonary valve side having a different blood flow axis.

As a result, because the two pieces of motion information, namely Vo' and Vs', have been obtained with respect to each of the positions on the annulus level of the pulmonary valve, corrected motion information Vc0 shall be defined by using any of the expressions explained in the first embodiment. After that, by using the expression Vo1+Vc0, the estimating function 172 calculates corrected motion information of each of the constituent points on the annulus level of the pulmonary valve, which corresponds to a lower part of the right ventricular outflow tract.

Subsequently, on the basis of the motion in the lower position (on the pulmonary valve level) of the right ventricular outflow tract, the estimating function 172 performs an extrapolation process on corrected motion on the crista supraventricularis (CSV) level corresponding to an upper position of the right ventricular outflow tract. In this situation, similarly to the example in the first embodiment, the motion information is obtained by using a rate of change in the length between predetermined positions. In the second embodiment, the position information of the site of the crista supraventricularis of which the motion has been obtained as described in the first embodiment shall be used without applying any modification thereto. In this situation, what requires position corrections with motion are boundary plane positions on the crista supraventricularis level other than the site of the crista supraventricularis. Accordingly, on the assumption that a rate of change in the length between the site of the crista supraventricularis and the pulmonary valve level is equal among the positions in the circumferential direction in the right ventricular outflow tract region, motion information for the extrapolation process is obtained. After that, an extrapolation process is performed for corrected motion of the positions on mutually-the-same circumference that correspond to one another between the mutually-different levels.

In that situation, at first, the estimating function 172 estimates the rate of change in the length between the pulmonary valve level and the crista supraventricularis. It should be noted that the corrected motion information is obtained by using the rate of change in the length. The reason is that, in some situations, the first site and the second site in the second embodiment may be the same as each other in certain positions on the crista supraventricularis level.

For this reason, the first site and the second site are distinguished from each other, by using the original motion V_CSVo of the site on the crista supraventricularis level as the first site and using V_CSV indicating the motion of the second site exhibited after applying the corrected motion information thereto as the second site.

In this situation, the original motion information will be defined. The component direction of the motion V_CSVo of the site on the CSV level in the second embodiment is expressed as Nt_CSV, as explained in the first embodiment. Accordingly, the motion V_CSVom resulting from a component separation can be expressed by using Expression (27) presented below. In this situation, V_CSVom corresponds to the motion information Vo' (Vo'=V_CSVom).

$$V\_CSVom = \langle V\_CSVo, Nt\_CSV \rangle * V\_CSVo \quad (27)$$

Subsequently, the motion information as in the second site is obtained by using a rate of change in the length between the pulmonary valve level and the crista supraventricularis level. As for the pulmonary valve level, the motion V21 expressed in Expression (28) presented below has been obtained for each of the points in the circumferential direction as a result of the abovementioned initial motion correction. In other words, the abovementioned corrected motion Vc0 is added to the original motion Vo1.

$$V21 = Vo1 + Vc0 \quad (28)$$

When V21 is expressed by using a position vector PV(i) on the pulmonary valve level, Expression (29) presented below is obtained (hereinafter, "i" denotes an arbitrary temporal phase). Accordingly, Expression (29) is equivalent to Expression (30) presented below.

$$V21 = PV\_in(N+1) - PV\_in(N) \quad (29)$$

$$PV\_in(N+1) = PV\_in(N) + V21 \quad (30)$$

Subsequently, as a new second site, a level above the pulmonary valve level in the region of the right ventricular outflow tract is selected. When the situation where this level is equal to the crista supraventricularis level is used as an example, the motion V_CSV on the crista supraventricularis level can be defined while using Expression (31) presented below by using a position vector CSV(i).

$$V\_CSV = CSV(N+1) - CSV(N) \quad (31)$$

In this situation, in the circumferential direction on the CSV level, at the constituent points of the crista supraventricularis, the values of CSV(N) and CSV(N+1) are both known. However, on the constituent points other than the crista supraventricularis, CSV(N+1) is unknown, although CSV(N) is known. For this reason, to calculate V_CSV in all the positions in the circumferential direction, the value of CSV(N+1), which is unknown, shall be determined.

The length |L1(N)| between the CSV level and the pulmonary valve level and the rate of change in the length L1SR(N) can be defined by using Expressions (32) to (34) presented below while using the position vectors thereof. In this situation, because |L1(N)| is determined by the position prior to the move, |L1(N)| is known.

$$L1(N+1) = PV(N+1) - CSV(N+1) \quad (32)$$

$$L1(N) = PV(N) - CSV(N) \quad (33)$$

$$L1SR(N) = (|L1(N+1)| - |L1(N)|)/|L1(N)| \quad (34)$$

When L1SR(N) at the crista supraventricularis is expressed as L1SR(N)_CSV, because the lengths |L1(N+1)_CSV| and |L1(N)_CSV| in that position are both known, Expression (25) presented below can be derived.

$$L1SR(N)\_CSV = (|L1(N+1)\_CSV| - |L1(N)\_CSV|)/|L1(N)\_CSV| \quad (35)$$

In contrast, in other positions, because an extrapolation process is performed with "L1SR(N)=L1SR(N)_CSV", Expression (36) presented below is satisfied on the basis of "L1SR(N)=L1SR(N)_CSV=(|L1(N+1)|-|L1(N)|)/|L1(N)|".

$$(L1SR(N)\_CSV+1)*|L1(N)| = |L1(N+1)| \quad (36)$$

Further, because it is possible to express L1(N+1) by using Expression (37) presented below, it is possible to calculate CSV(N+1) by using Expression (38) presented below.

$$L1(N+1) = PV\_in(N+1) - CSV(N+1) \quad (37)$$

$$CSV(N+1) = PV\_in(N+1) - (L1SR(N)\_CSV+1)*L1(N) \quad (38)$$

Because PV_in (N+1) has already been obtained, V_CSV is determined by the expression above. After that, the motion component V_CSVm resulting from a component separation can be expressed by using Expression (39) presented below while using the direction vector Nt_CSV on the CSV level. The motion component V_CSVm corresponds to corrected motion information Vs' transferred from the second site to the first site (Vs'=V_CSVm).

$$V\_CSVm = \langle V\_CSV, Nt\_CSV \rangle * V\_CSV \quad (39)$$

Accordingly, because the two pieces of motion information, namely Vo' and Vs' have been obtained with respect to the positions on the CSV level, Vc1 can be defined by using one of the settings in the expressions explained in the first embodiment.

After that, the estimating function 172 calculates corrected motion information with respect to the entire region of the right ventricular outflow tract by performing an interpolation process between the levels, while using the corrected motion Vc1 on the CSV level obtained at this time and the corrected motion information Vc0 on the annulus level of the pulmonary valve obtained previously. After that, the estimating function 172 corrects the motion of the entire region of the right ventricular outflow tract, by using the calculated corrected motion information.

As explained above, the estimating function 172 according to the second embodiment is configured to perform the extrapolation process in the upper part of the right ventricular outflow tract, after performing the extrapolation process to interpolate the motion information of the annulus site of the aortic valve, into the annulus site of the pulmonary valve at the lower end of the right ventricular outflow tract. For example, when the second site is the aortic valve, the estimating function 172 is configured to calculate the third motion information of the other points on the circumference on the pulmonary valve level, by performing the extrapolation process while using the first motion information at one point of the right ventricular outflow tract on the pulmonary valve level and the second motion information at the annulus site of the aortic valve. After that, by performing the extrapolation process while using the first motion information and the third motion information calculated on the circumference on the pulmonary valve level, the estimating function 172 calculate the fourth motion information of each of the points on the circumference of the right ventricular outflow tract on the crista supraventricularis level. As a result, by using at least one selected from between the crista supraventricularis and the aortic valve annulus as the second site, the estimating function 172 according to the second embodiment is able to correct the motion information of all the points of the right ventricular outflow tract.

More specifically, the estimating function 172 performs the extrapolation process to interpolate the corrected motion information obtained from the first motion information of the pulmonary valve annulus site and the second motion information of the aortic valve annulus site in the lower end part of the right ventricular outflow tract, into the pulmonary valve annulus site in the lower end part of the right ventricular outflow tract. Subsequently, the estimating function 172 makes a correction by performing the extrapolation process on the upper part of the right ventricular outflow tract, while using the corrected motion information obtained by using the motion information of the lower end part of the right ventricular outflow tract corrected by the extrapolation process as a new piece of second motion information and using the motion information of the upper part of the right ventricular outflow tract as a new piece of first motion information.

Further, for example, the estimating function 172 is configured to set the annulus site of the aortic valve and to further calculate the motion information of the annulus site of the aortic valve that was set by performing the process including the template matching process. For example, the estimating function 172 sets the initial position of the annulus site of the aortic valve by implementing either the first setting method or the second setting method explained above. After that, the estimating function 172 obtains the motion of the position of the annulus site of the aortic valve between the temporal phases by performing the three-dimensional speckle tracking process. As a result, the estimating function 172 is able to use the points positioned on the outside of the right ventricular outflow tract as the second site.

Third Embodiment

In the first and the second embodiments described above, the example is explained in which, as the site that is positioned in the vicinity of the right ventricular outflow tract and exhibits motion similar to that of the right ventricular outflow tract, either the crista supraventricularis or the aortic valve is individually used; however, possible embodiments are not limited to this example. For instance, the ultrasound diagnosis apparatus 1 is able to correct the motion information of the right ventricular outflow tract by using the pieces of motion information of both the crista supraventricularis and the aortic valve each serving as a site that is positioned in the vicinity of the right ventricular outflow tract and exhibits motion information similar to that of the right ventricular outflow tract.

The ultrasound diagnosis apparatus 1 according to the third embodiment has the same configuration as that of the ultrasound diagnosis apparatus 1 illustrated in FIG. 1, except that a part of the processes performed by the estimating function 172 is different. The third embodiment will therefore be explained while a focus is placed on the differences from the first embodiment. The explanation of some of the elements having the same functions as those in the first embodiment will be omitted.

In the third embodiment, at first, the motion correction amount V_AV is calculated as explained in the second embodiment for the purpose of correcting the motion information of the annulus site of the pulmonary valve of the right ventricular outflow tract, on the basis of the motion information of the annulus site of the aortic valve. Subsequently, as explained in the first embodiment, on the basis of the motion information of the crista supraventricularis, the motion correction amount V_CSV is calculated for the annulus site of the pulmonary valve corresponding to the lowermost level of the right ventricular outflow tract. After that, by using both of the pieces of motion correction information, namely V_AV and V_CSV, combined motion information V_PV to be used for actually correcting the annulus site of the pulmonary valve is calculated. In this situation, as specific examples of defining V_PV, there are primarily two methods called a first calculation method and a second calculation method, as described below.

To begin with, the first calculation method will be explained. According to the first calculation method, the estimating function 172 defines the combined motion information by calculating a weighted average of the motion values. For example, by using Expression (40) presented below, the estimating function 172 calculates V_PV. In Expression (40), α denotes a coefficient satisfying "0≤α≤1".

$$V\_PV = \alpha * V\_AV + (1-\alpha) * V\_CSV \qquad (40)$$

In Expression (40), when α=0.5 is satisfied, the simplest method is obtained. This situation corresponds to making a correction by using an average motion value of the two, namely V_AV and V_CSV.

Generally speaking, a method is known by which control is exercised in accordance with estimated quality of the two pieces of motion information while arranging α to be variable. In that situation, as the estimated quality, it is acceptable to use a publicly-known index value used in techniques for speckle tracking processes based on pattern matching processes (e.g., a value obtained by performing a weighted addition or the like using a plurality of index values each of which is in a correlational relation with quality of motion, such as brightness values of the target site, spatial dispersion values of the brightness levels, or correlational coefficient values used during pattern matching processes or the like; See Patent document 1: Japanese Patent Application Laid-open No. 2014-121541). Further, by using a quality index value Q_AV of the annulus site of the pulmonary valve and a quality index value Q_CSV of the site of the crista supraventricularis, the coefficient α is calculated by using Expression (41) presented below, for example. In this situation, it is assumed that Q_AV and Q_CSV are each standardized so as to have a value in the range from 0 to 1.

$$\alpha = \begin{cases} Q\_AV/(Q\_AV+Q\_CSV) & \text{(when } Q\_AV+Q\_CSV \neq 0) \\ 0.5 & \text{(when } Q\_AV+Q\_CSV = 0) \end{cases} \qquad (41)$$

As a result, of the two pieces of motion information, namely V_AV and V_CSV, it is expected that the obtained motion correction information has a larger weight on the motion information estimated to have the higher level of motion quality. It is therefore possible to achieve a robust motion correction with respect to the image quality condition that is input.

Next, the second calculation method will be explained. According to the second calculation method, the motion amounts of the two, namely V_AV and V_CSV, are compared with each other so as to define the larger of the two as the combined motion information. In the first calculation method, the manner in which the information is combined is controlled in accordance with the estimated quality of the motion information, which serves as the "input condition" under which the motion was obtained. In contrast, according to the second calculation method, the obtained pieces of "motion output information" themselves are compared with each other. In other words, the larger of the two, namely |V_AV| and |V_CSV|, is selected to be used as the combined motion information.

$$V\_PV = \begin{cases} V\_CSV & \text{(when } |V\_AV| \leq |V\_CSV|) \\ V\_AV & \text{(when } |V\_AV| > |V\_CSV|) \end{cases} \qquad (42)$$

According to the second calculation method, on the assumption that the motion values obtained from both V_AV and V_CSV are supposed to have approximately the same magnitude as each other, it is considered that the information having the larger motion amount reflects the actual motion more accurately with respect to the image quality condition that is input. An advantage of using the second calculation method instead of the first calculation method is that it is possible to avoid the restrictions that are imposed by the actual estimation of the motion quality indices. For example, it is difficult to distinguish echo signals that do not stably fluctuate (e.g., multiple reflection artifacts) from echo signals acquired from the actual target tissue. In that situation, although a quality index value may be large, because there is almost zero motion, the value of V_PV can be underestimated when such an artifact is present in one of the sites. According to the second calculation method, however, it is possible to obtain a more appropriate value as V_PV even in those situations, independently of the estimated quality of the motion information.

As explained above, by using either the first calculation method or the second calculation method, the estimating function 172 calculates the motion correction amount V_PV of the annulus site of the pulmonary valve in the right ventricular outflow tract. After that, the estimating function 172 can provide the motion correction amount for the other points of the right ventricular outflow tract through the extrapolation process, by performing either the extrapolation process on the motion based on the crista supraventricularis as explained in the first embodiment or the extrapolation process on the motion based on the annulus site of the aortic valve as explained in the second embodiment.

In that situation, as for the selection of the site used for the extrapolation process, the site for which the motion information has a higher level of estimated quality shall be selected when the first calculation method is used. The site on which the judgment is made in the selection of V_PV shall be selected when the second calculation method is used.

As explained above, in the ultrasound diagnosis apparatus 1 according to the third embodiment, when the crista supraventricularis and the aortic valve are used as the second site, the estimating function 172 calculates the second motion information by combining the motion information obtained from the crista supraventricularis with the motion information obtained from the aortic valve. More specifically, the estimating function 172 calculates, as the second motion information, one selected from between: the motion information based on the weighted averaging process that uses the weight defined by using the quality index about the motion obtained from the crista supraventricularis and the aortic valve; and whichever has motion of a larger magnitude between the motion information obtained from the crista supraventricularis and the motion information obtained from the aortic valve. As a result, the ultrasound diagnosis apparatus 1 according to the third embodiment is able to correct the motion information of the right ventricular outflow tract, by using the pieces of motion information of both the crista supraventricularis and the aortic valve.

Other Embodiments

In addition to the embodiments described above, it is possible to carry out the present disclosure in other various modes.

A Medical Image Processing Apparatus

For instance, in the embodiments above, the example is explained in which the processes described above are performed by the ultrasound diagnosis apparatus 1; however, possible embodiments are not limited to this example. For instance, after the volume data acquired by the ultrasound diagnosis apparatus 1 is transferred to a medical image processing apparatus such as a workstation, the processes described above may be executed by the medical image processing apparatus.

Further, the constituent elements of the apparatuses illustrated in the drawings are based on functional concepts. Thus, it is not necessary to physically configure the constituent elements as indicated in the drawings. In other words, the specific modes of distribution and integration of the apparatuses are not limited to those illustrated in the drawings. It is acceptable to functionally or physically distribute or integrate all or a part of the apparatuses in any arbitrary units, depending on various loads and the status of use. Further, all or an arbitrary part of the processing functions performed by the apparatuses may be realized by a CPU and a computer program analyzed and executed by the CPU or may be realized as hardware using wired logic.

Further, with regard to the processes explained in the embodiments above, it is acceptable to manually perform all or a part of the processes described as being performed automatically. Conversely, by using a method that is publicly known, it is also acceptable to automatically perform all or a part of the processes described as being performed manually. Further, unless noted otherwise, it is acceptable to arbitrarily modify any of the processing procedures, the controlling procedures, specific names, and various information including various types of data and parameters that are presented in the above text and the drawings.

It is possible to realize the medical image processing methods described in the embodiments above by causing a medical image processing program prepared in advance to be executed by a computer such as a personal computer, a workstation, or the like. The medical image processing method may be distributed via a network such as the Internet. Further, the medical image processing method may be recorded onto a computer-readable recording medium such as a hard disk, a flexible disk (FD), a Compact Disk Read-Only Memory (CD-ROM), a magneto-optical (MO) disk, a Digital Versatile Disk (DVD), or the like, so as to be executed as being read from the recording medium by a computer.

The term "processor" used in the above explanation denotes, for example, a Central Processing Unit (CPU), a Graphics Processing Unit (GPU), or a circuit such as an Application Specific Integrated Circuit (ASIC) or a programmable logic device (e.g., a Simple Programmable Logic Device [SPLD], a Complex Programmable Logic Device [CPLD], or a Field Programmable Gate Array [FPGA]). The one or more processors realize the functions thereof by reading the computer programs (hereinafter, "programs") stored in the internal storage 160 and executing the read programs. Instead of storing the programs into the internal storage 160, it is also acceptable to directly incorporate the programs into the circuits of the one or more processors. In that situation, the one or more processors realize the functions thereof by reading the programs incorporated in the circuits thereof and executing the read programs. The processors disclosed in the embodiments do not each necessarily have to be structured as a single circuit. It is also acceptable to structure one processor by combining together a plurality of independent circuits so as to realize the functions thereof. Further, it is also acceptable to integrate two or more of the constituent elements illustrated in the drawings into one processor so as to realize the functions thereof.

According to at least one aspect of the embodiments described above, it is possible to improve the quality of the analyses performed on the motion of the right ventricular outflow tract.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasound diagnosis apparatus comprising processing circuitry configured to:
    obtain volume data corresponding to at least one cardiac cycle and being taken of a region including a right ventricle of a patient;

estimate motion information of a tissue in the region by using the volume data;

calculate corrected motion information of the tissue by correcting, from the estimated motion information, first motion information of a right ventricular outflow tract, which is an outflow tract of the right ventricle, by using second motion information corresponding to a site that is at least one selected from between a crista supraventricularis and an aortic valve;

calculate wall motion information related to the right ventricle, on a basis of the corrected motion information of the tissue; and output the calculated wall motion information related to the right ventricle.

2. The ultrasound diagnosis apparatus according to claim 1, wherein the processing circuitry corrects motion information that is a part of the first motion information and is related to a component in a contour direction of a tissue parallel to a blood flow direction, by using motion information that is a part of the second motion information and is related to a component in a contour direction of a tissue parallel to a blood flow direction.

3. The ultrasound diagnosis apparatus according to claim 1, wherein the processing circuitry corrects the first motion information by using a spatial extrapolation process.

4. The ultrasound diagnosis apparatus according to claim 1, wherein the processing circuitry calculates the corrected motion information used for correcting the first motion information, based on a difference between the first motion information and the second motion information.

5. The ultrasound diagnosis apparatus according to claim 4, wherein the processing circuitry adds the corrected motion information to the first motion information.

6. The ultrasound diagnosis apparatus according to claim 4, wherein
the processing circuitry compares a magnitude of the first motion information with a magnitude of the second motion information,
when the magnitude of the first motion information is larger, the processing circuitry arranges the corrected motion information to be zero, and
when the magnitude of the first motion information is smaller, the processing circuitry adjusts the corrected motion information based on the magnitude of the first motion information and the magnitude of the second motion information.

7. The ultrasound diagnosis apparatus according to claim 1, wherein, when the site is the crista supraventricularis, the processing circuitry calculates third motion information of one point of the right ventricular outflow tract on a pulmonary valve level by performing an extrapolation process while using the second motion information and further calculates fourth motion information of another point of the right ventricular outflow tract on the pulmonary valve level by performing an extrapolation process while using the calculated third motion information.

8. The ultrasound diagnosis apparatus according to claim 1, wherein,
when the site is the aortic valve,
by performing an extrapolation process that uses the first motion information at one point of the right ventricular outflow tract on a pulmonary valve level and the second motion information of an annulus site of the aortic valve, the processing circuitry calculates third motion information of another point on a circumference on the pulmonary valve level, and by performing an extrapolation process that uses the first motion information and the third motion information on the circumference on the pulmonary valve level that were calculated, the processing circuitry calculates fourth motion information of each of points on a circumference of the right ventricular outflow tract on a crista supraventricularis level.

9. The ultrasound diagnosis apparatus according to claim 8, wherein the processing circuitry sets the annulus site of the aortic valve and calculates motion information of the set annulus site of the aortic valve by performing a process including a pattern matching process.

10. The ultrasound diagnosis apparatus according to claim 8, wherein the processing circuitry uses, as the second motion information, a motion information component in a blood vessel axial direction of an aorta with respect to the annulus site of the aortic valve.

11. The ultrasound diagnosis apparatus according to claim 1, wherein the processing circuitry calculates the second motion information by using at least one selected from between: a rate of change in a length between a cardiac apex of the right ventricle and the site; and a rate of change in a length between the site and a point that is positioned in a vicinity of the site and is positioned in a direction substantially parallel to the right ventricular outflow tract.

12. The ultrasound diagnosis apparatus according to claim 1, wherein, when the crista supraventricularis and the aortic valve are used as the site, the processing circuitry calculates the second motion information by combining together motion information obtained from the crista supraventricularis and motion information obtained from the aortic valve.

13. The ultrasound diagnosis apparatus according to claim 12, wherein the processing circuitry calculates, as the second motion information, one selected from between: motion information based on a weighted averaging process that uses a weight defined by using a quality index about motion obtained from the crista supraventricularis and the aortic valve; and whichever has motion of a larger magnitude between the motion information obtained from the crista supraventricularis and the motion information obtained from the aortic valve.

14. A medical image processing apparatus comprising processing circuitry configured to:
obtain volume data corresponding to at least one cardiac cycle and being taken of a region including a right ventricle of a patient;
estimate motion information of a tissue in the region by using the volume data;
calculate corrected motion information of the tissue by correcting, from the estimated motion information, first motion information of a right ventricular outflow tract, which is an outflow tract of the right ventricle, by using second motion information corresponding to a site that is at least one selected from between a crista supraventricularis and an aortic valve;
calculate wall motion information related to the right ventricle, on a basis of the corrected motion information of the tissue; and
output the calculated wall motion information related to the right ventricle.

15. A medical image processing method comprising:
obtaining volume data corresponding to at least one cardiac cycle and being taken of a region including a right ventricle of a patient;
estimating motion information of a tissue in the region by using the volume data;

calculating corrected motion information of the tissue by correcting, from the estimated motion information, first motion information of a right ventricular outflow tract, which is an outflow tract of the right ventricle, by using second motion information corresponding to a site that is at least one selected from between a crista supraventricularis and an aortic valve;

calculating wall motion information related to the right ventricle, on a basis of the corrected motion information of the tissue; and outputting the calculated wall motion information related to the right ventricle.

* * * * *